US011000656B2

(12) United States Patent
Gholami et al.

(10) Patent No.: US 11,000,656 B2
(45) Date of Patent: May 11, 2021

(54) CLINICAL DECISION SUPPORT SYSTEM FOR PATIENT-VENTILATOR ASYNCHRONY DETECTION AND MANAGEMENT

(71) Applicant: Autonomous Healthcare, Inc., Hoboken, NJ (US)

(72) Inventors: Behnood Gholami, Hoboken, NJ (US); Timothy S. Phan, Brooklyn, NY (US)

(73) Assignee: Autonomous Healthcare, Inc., Hoboken, NJ (US)

( * ) Notice: Subject to any disclaimer, the term of this patent is extended or adjusted under 35 U.S.C. 154(b) by 0 days.

(21) Appl. No.: 17/014,778

(22) Filed: Sep. 8, 2020

(65) Prior Publication Data

US 2020/0405987 A1    Dec. 31, 2020

Related U.S. Application Data

(63) Continuation of application No. 16/762,224, filed as application No. PCT/US2018/060056 on Nov. 9, 2018.

(Continued)

(51) Int. Cl.
*A61M 16/00* (2006.01)
*G16H 20/40* (2018.01)

(52) U.S. Cl.
CPC ........ *A61M 16/024* (2017.08); *A61M 16/026* (2017.08); *G16H 20/40* (2018.01);
(Continued)

(58) Field of Classification Search
CPC .............. A61M 16/00; A61M 16/0051; A61M 16/024; A61M 16/026; A61M 2016/0018; A61M 2016/0021; A61M 2016/0027; A61M 2016/0033; A61M 2016/0036; A61M 2016/0039; A61M 2205/3331; A61M 2205/3334; A61M 2205/3344; A61M 2205/502; A61M 2205/52; A61B 5/08; A61B 5/087; A61B 5/091
See application file for complete search history.

(56) References Cited

U.S. PATENT DOCUMENTS 7,212,850 B2    5/2007  Prystowsky et al.
7,907,996 B2    3/2011  Prystowsky et al.
(Continued)

FOREIGN PATENT DOCUMENTS

AU    2018366291 B2    9/2020
WO    2017068464 A1    4/2017
WO    2019094736 A1    5/2019

OTHER PUBLICATIONS (Gholami, Behnood et al.) Co-pending U.S. Appl. No. 16/762,224, filed May 7, 2020, Specification, Claims, and Figures.
(Continued)

*Primary Examiner* — Joseph D. Boecker
(74) *Attorney, Agent, or Firm* — New River Valley IP Law, P.C.; Michele L. Mayberry

(57) ABSTRACT

The present disclosure describes a system that automatically detects patient-ventilator asynchrony and trends in patient-ventilator asynchrony. The present disclosure describes a framework that uses pressure, flow, and volume waveforms to detect patient-ventilator asynchrony and the presence of secretions in the ventilator circuit.

20 Claims, 23 Drawing Sheets

Related U.S. Application Data

(60) Provisional application No. 62/583,558, filed on Nov. 9, 2017.

(52) U.S. Cl.
CPC ............... *A61M 2016/0027* (2013.01); *A61M 2016/0033* (2013.01); *A61M 2205/3379* (2013.01); *A61M 2205/3584* (2013.01); *A61M 2205/502* (2013.01); *A61M 2205/52* (2013.01)

(56) References Cited

U.S. PATENT DOCUMENTS

| | | | |
|---|---|---|---|
| 8,920,333 B2 | 12/2014 | Younes | |
| 9,027,552 B2 | 5/2015 | Angelico et al. | |
| 9,392,964 B2 | 7/2016 | Mulqueeny et al. | |
| 10,874,811 B2 | 12/2020 | Gholami et al. | |
| 2008/0110461 A1* | 5/2008 | Mulqueeny | A61B 5/0871 128/204.23 |
| 2009/0107502 A1* | 4/2009 | Younes | A61M 16/026 128/204.23 |
| 2011/0297155 A1 | 12/2011 | Shelly et al. | |
| 2012/0167885 A1 | 7/2012 | Masic et al. | |
| 2014/0012150 A1 | 1/2014 | Milne et al. | |
| 2014/0034054 A1* | 2/2014 | Angelico | A61M 16/0003 128/204.23 |
| 2014/0053840 A1 | 2/2014 | Liu | |
| 2014/0060539 A1 | 3/2014 | Korten | |
| 2014/0276173 A1* | 9/2014 | Banner | A61M 16/0833 600/533 |
| 2015/0013674 A1 | 1/2015 | Doyle et al. | |
| 2015/0090258 A1 | 4/2015 | Milne et al. | |
| 2016/0279361 A1* | 9/2016 | Mulqueeny | A61M 16/06 |
| 2018/0304034 A1* | 10/2018 | Vicario | A61M 16/026 |
| 2018/0317808 A1 | 11/2018 | Wang et al. | |
| 2019/0371460 A1 | 12/2019 | Gutierrez | |
| 2020/0054520 A1 | 2/2020 | Johnson et al. | |
| 2020/0261674 A1* | 8/2020 | Gholami | G16H 20/40 |

OTHER PUBLICATIONS (Gholami, Behnood et al.) Co-pending Australian Application No. 2018366291, filed May 22, 2020, Specification, Claims, Figures, 66 pages.
(Gholami, Behnood et al.) Co-pending European Application No. 18876990.5, filed Jun. 3, 2020, Specification (see PCT/US18/60056) and Claims.
(Gholami, Behnood et al.) Co-pending International Application No. PCT/US18/60056, filed Nov. 9, 2018, Specification, Claims, Figures.
Autonomous Healthcare Announces Successful Completion of a Validation Study for Its Automated Patient-Ventilator Asynchrony Detection Technology, Dec. 18, 2019, Cision PR Newswire.
Blanch, Lluis, et al. "Asynchronies during mechanical ventilation are associated with mortality." Intensive care medicine 41.4 (2015): 633-641.
Blanch, Lluis, et al. "Validation of the Better Care® system to detect ineffective efforts during expiration in mechanically ventilated patients: a pilot study." Intensive care medicine 38.5 (2012): 772-780.
Breiman, Leo "Random Forests." Statistics Department, University of California, Jan. 2001, 33 pages.
Breiman, Leo. "Random Forests." Machine Learning, 45, 5-32, 2001.
Carlucci, Annalisa et al. "Patient-ventilator asynchronies: may the respiratory mechanics play a role?" Critical Care, 2013, 17:R54, 8 pages.
Chang, Lan, Pau-Choo Chung, and Chang Wen Chen. "Combining Neural Network and Wavelet Transform for Trigger Asynchrony Detection." CIBCB. 2007.
Chanques, Gerald, et al. "Impact of ventilator adjustment and sedation-analgesia practices on severe asynchrony in patients ventilated in assist-control mode." Critical care medicine 41.9 (2013): 2177-2187.
Chao, David C., David J. Scheinhorn, and Meg Stearn-Hassenpflug. "Patient-ventilator trigger asynchrony in prolonged mechanical ventilation." Chest 112.6 (1997): 1592-1599.
Chen, Chang-Wen, et al. "Detecting ineffective triggering in the expiratory phase in mechanically ventilated patients based on airway flow and pressure deflection: feasibility of using a computer algorithm." Critical care medicine 36.2 (2008): 455-461.
Cohen, Jacob "A Coefficient of Agreement for Nominal Scales." Educational and Psychological Measurement, vol. XX, No. 1, 1960, 37-46.
Colombo, Davide, et al. "Efficacy of ventilator waveforms observation in detecting patient-ventilator asynchrony." Critical care medicine 39.11 (2011): 2452-2457.
Colombo, Davide, et al. "Physiologic response to varying levels of pressure support and neurally adjusted ventilatory assist in patients with acute respiratory failure." Intensive care medicine 34.11 (2008): 2010.
Co-pending U.S. Appl. No. 16/762,224, Non-Final Office Action, dated Jul. 27, 2020, 17 pages.
Co-pending U.S. Appl. No. 16/762,224, Preliminary Amendment, filed May 7, 2020, 10 pages.
Co-pending Australian Application No. 2018366291, Claims as Accepted, dated Jul. 31, 2020, 4 pages.
Co-pending Australian Application No. 2018366291, Examination Report No. 1, dated Jul. 23, 2020, 8 pages.
Co-pending Australian Application No. 2018366291, Notice of Acceptance, dated Aug. 20, 2020, 3 pages.
Co-pending Australian Application No. 2018366291, Response to Examination Report No. 1, filed Jul. 31, 2020, 76 pages.
Co-pending International Application No. PCT/US18/60056, Invitation to Pay Additional Fees dated Jan. 25, 2019, 3 pages.
Co-pending International Application No. PCT/US18/60056, Search Report and Written Opinion, dated Mar. 21, 2019, 11 pages.
De Haro, Candelaria, et al. "Patient-ventilator asynchronies during mechanical ventilation: current knowledge and research priorities." Intensive care medicine experimental 7.1 (2019): 43.
De Wit, Marjolein et al. "Observational study of patient-ventilator asynchrony and relationship to sedation level." Journal of Critical Care (2009) 24, 74-80.
De Wit, Marjolein, et al. "Ineffective triggering predicts increased duration of mechanical ventilation." Critical care medicine 37.10 (2009): 2740-2745.
De Wit, Marjolein. "Monitoring of patient-ventilator interaction at the bedside." Respiratory care 56.1 (2011): 61-72.
Dres, M., Rittayami, N., Brochard, L., Monitoring patient-ventilator asynchrony, Curr. Opin. Crit. Care 22 (2016) 246-253.
Epstein, Scott K. "How Often Does Patient-Ventilator Asynchrony Occur and What are the Consequences?" Respiratory Care, Jan. 2011, vol. 56, No. 1, 25-38.
Garg, Amit X. et al. "Effects of Computerized Clinical Decision Support Systems on Practitioner Performance and Patient Outcomes: A Systematic Review." Journal of the American Medical Association, Mar. 9, 2005, vol. 293, No. 10, 1223-1238.
Gholami et al. "Replicating human expertise of mechanical ventilation waveform analysis in detecting patient-ventilator cycling asynchrony using machine learning." Computers in Biology and Medicine, vol. 97, 2018, pp. 137-144, ISSN 0010-4825, https://doi.org/10.1016/j.compbiomed.2018.04.016.
Gholami, Behnood et al., "Replicating human expertise of mechanical ventilation waveform analysis in detecting patient-ventilator cycling asynchrony using machine learning," Computers in Biology and Medicine 97 (2018) 137-144.
Girard, Timothy D. et al. "Efficacy and safety of a paired sedation and ventilator weaning protocol for mechanically ventilated patients in intensive care (Awakening and Breathing Controlled trial): a randomised controlled trial." Lancet, 2008, 371: 126-134.
Guglielminotti, Jean et al. "Bedside Detection of Retained Tracheobronchial Secretions in Patients Receiving Mechanical Ventilation." Chest, 118, 4, Oct. 2000, 1095-1099.

(56) References Cited

OTHER PUBLICATIONS

Gutierrez, Guillermo, et al. "Automatic detection of patient-ventilator asynchrony by spectral analysis of airway flow." Critical Care 15.4 (2011): R167.
Haddad, Wassim M., et al. "Clinical decision support and closed-loop control for intensive care unit sedation." Asian Journal of Control 15.2 (2013): 317-339.
Horng, Steven et al. "Creating an automated trigger for sepsis clinical decision support at emergency department triage using machine learning." PLOS One, Apr. 6, 2017, 1-16.
Hunt, DL et al. "Effects of computer-based clinical decision support systems on physician performance and patient outcomes: a systematic review." Journal of the American Medical Association, Oct. 21, 1998; 280(15):1339-1346.
Jubran, Amal et al. "Use of Flow-Volume Curves in Detecting Secretions in Ventilator-dependent Patients." Am J Respir Crit Care Med vol. 150, pp. 766-769, 1994.
Kondili, Eumorfia, et al. "Identifying and relieving asynchrony during mechanical ventilation." Expert review of respiratory medicine 3.3 (2009): 231-243.
Kress, John P. et al. "Daily Interruption of Sedative Infusions in Critically Ill Patients Undergoing Mechanical Ventilation." The New England Journal of Medicine, vol. 342, No. 20, May 18, 2000, 1471-1477.
Landis, J. Richard et al. "The Measurement of Observer Agreement for Categorical Data." Biometrics, Mar. 1977, 33, 159-174.
Leclerc, F. et al. "Use of the flow-volume loop to detect secretions in ventilated children." Intensive Care Medicine, 22, 88 (1995).
Li, Hancao, and Wassim M. Haddad. "Optimal determination of respiratory airflow patterns using a nonlinear multicompartment model for a lung mechanics system." Computational and mathematical methods in medicine 2012 (2012).
Mellott, Karen G. et al. "Patient-Ventilator Dyssynchrony Clinical Significance and Implications for Practice." Critical Care Nurse, vol. 29, No. 6, Dec. 2009, 41-55.
Mulqueeny, Qestra, et al. "Automated detection of asynchrony in patient-ventilator interaction." 2009 Annual International Conference of the IEEE Engineering in Medicine and Biology Society. IEEE, 2009.
Nilsestuen, Jon O. et al. "Using Ventilator Graphics to Identify Patient-Ventilator Asynchrony." Respiratory Care, Feb. 2005, vol. 50, No. 2, 202-234.
Phan, Timothy S., et al. "Validation of an automated system for detecting ineffective triggering asynchronies during mechanical ventilation: a retrospective study" Journal of Clinical Monitoring and Computing (2019): 1-5.
Reade, Michael C. et al. "Sedation and Delirium in the Intensive Care Unit." The New England Journal of Medicine, 2014, 370:444-454.
Robinson, Bryce R.H. et al. "Patient-Ventilator Asynchrony in a Traumatically Injured Population." Respiratory Care, Nov. 2013, vol. 58, No. 11, 1847-1855.
Schweickert, William D. et al. "Early physical and occupational therapy in mechanically ventilated, critically ill patients: a randomised controlled trial." Lancet, 2009, 373:1874-1882.
Thille, Arnaud W., et al. "Patient-ventilator asynchrony during assisted mechanical ventilation." Intensive care medicine 32.10 (2006): 1515-1522.
Vicario, Francesco et al. "Noninvasive Estimation of Respiratory Mechanics in Spontaneously Breathing Ventilated Patients: A Constrained Optimization Approach." IEEE Transactions on Biomedical Engineering, vol. 63, No. 4, Apr. 2016, 775-787.
Vignaux, Laurence et al. "Patient-ventilatory asynchrony during non-invasive ventilation for acute respiratory failure: a multicenter study." Intensive Care Med (2009) 35:840-846.
Vignaux, Lawrence et al. "Performance of noninvasive ventilation algorithms on ICU ventilators during pressure support: a clinical study." Intensive Care Med (2010) 36:2053-2059.
Wyner, Abraham J., et al. "Explaining the success of adaboost and random forests as interpolating classifiers." The Journal of Machine Learning Research 18.1 (2017): 1558-1590.
Younes, Magdy, et al. "A method for monitoring and improving patient: ventilator interaction." Intensive care medicine 33.8 (2007): 1337-1346.
Co-pending U.S. Appl. No. 16/762,224, Final Office Action, dated Oct. 30, 2020, 10 pages.
Co-pending U.S. Appl. No. 16/762,224, Notice of Allowance, dated Nov. 16, 2020, 7 pages.
Co-pending U.S. Appl. No. 16/762,224, Response to Final Office Action filed Nov. 9, 2020, 8 pages.
Co-pending U.S. Appl. No. 16/762,224, Response to Non-Final Office Action filed Oct. 13, 2020, 13 pages.
Co-pending European Application No. 18876990.5, Amended Claims, filed Jun. 3, 2020, 4 pages.

\* cited by examiner

CLINICAL DECISION SUPPORT SYSTEM FOR PATIENT-VENTILATOR ASYNCHRONY DETECTION AND MANAGEMENT

CROSS-REFERENCE TO RELATED APPLICATIONS

This application is a Continuation application of U.S. application Ser. No. 16/762,224, filed May 7, 2020, which application is a National Stage application under 35 U.S.C. § 371 of International Application No. PCT/US18/60056, filed Nov. 9, 2018, which application relies on the disclosure of and claims priority to and the benefit of the filing date of U.S. Provisional Application No. 62/583,558, filed Nov. 9, 2017, the disclosure of which is incorporated by reference herein in its entirety.

GOVERNMENT RIGHTS

This invention was made with the support of the United States Government under Grant number IIP-1456404 by the National Science Foundation. The United States Government has certain rights in the invention.

BACKGROUND

Patient-ventilator asynchrony, also referred to as dyssynchrony, refers to a mismatch between ventilator delivery and patient demand. To address patient-ventilator asynchrony, clinicians can adjust ventilator settings or ventilation modes, change a patient's sedation level, or perform other interventions. However, continuous monitoring of mechanically ventilated patients by clinical staff is infeasible.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

The present invention provides methods and systems for detecting patient-ventilator asynchrony. One method describes how to calculate a waveform from mechanical ventilator pressure and flow waveforms that indicates patient-ventilator interactions whereby a plurality of peaks and valleys of the resulting waveform indicates asynchronous patient-ventilator interactions. Then a method is described that uses said calculated patient-ventilator interaction indicator waveform to determine various types of patient-ventilator asynchrony types. This method comprises using a collection of ventilator pressure and flow waveforms from prior patients and/or through generating a plurality of synthetic ventilator pressure and flow waveforms, calculating said interaction indicator waveform for each individual breath cycle of the synthetic waveforms, extracting features from the interaction indicator waveform, and training a machine learning algorithm to perform mapping between features and patient-ventilator asynchrony types. Training data typically involves assigning labels associated with different asynchrony types to waveforms from each breath. In the case of using prior patient data for training, such labels can be generated by clinical experts reviewing the waveforms or by clinical experts reviewing waveforms as well as other appropriate clinical signals such as esophageal pressure or diaphragm activity. In the case of using synthetic data, actual asynchrony type is known a priori when generating such synthetic waveforms. A system is also described that acquires ventilator pressure and flow waveform data from a data source, generates said interaction indicator waveform from the waveform data received, extracts a set of features from said indicator waveform, and classifies each individual breath cycle into categories of patient-ventilator asynchrony. The systems and methods can also be configured to include recommendation, alert, and/or notification modules or steps to notify end user(s) such as clinicians in a manner sufficient to address the asynchrony and/or adjust ventilator settings to avoid asynchrony, assess a patient experiencing asynchrony and make an appropriate action, alert hospital staff to, and/or change internal settings automatically, optimize or improve ventilator performance (e.g., triggering and cycling timings), or identify other relevant parameters that affect ventilator function, and/or to allow for intervention including changes to a patient's sedation level. The systems and methods can be implemented on a peripheral device communicating with a ventilator or embedded in a ventilator.

An embodiment described of the system further includes a graphical user interface (GUI) for communicating detected patient-ventilator asynchrony whereby the system can be used as a clinical decision support system. In some embodiments, the GUI can display educational information on the detected asynchronies to further assist in managing mechanically ventilated patients.

According to a first aspect of the invention, there is provided system for detecting patient ventilator interaction comprising:

a detection module comprising computer executable instructions in operable communication with one or more computer processor, the detection module configured for and in operable communication with a ventilator for acquiring mechanical ventilator airway pressure, flow, and/or volume waveform data; and a patient ventilator interaction indicator module in operable communication with the detection module, the patient ventilator interaction indicator module comprising computer executable instructions in operable communication with one or more computer processor for:

generating a patient ventilator interaction indicator waveform comprising a Delta waveform from said ventilator waveform data, wherein the Delta waveform represents the difference between normalized pressure, after correcting for positive end expiratory pressure (PEEP), and normalized flow waveforms;

extracting a set of features from said patient ventilator interaction indicator waveform; and determining and indicating a type of patient ventilator asynchrony present, or absence thereof, associated with one or more breath cycle, which patient ventilator asynchrony or absence thereof is based on the extracted set of features.

BRIEF DESCRIPTION OF THE DRAWINGS

It should be noted in the following description that like or the same reference numerals in different embodiments denote the same or similar features.

Notwithstanding any other forms which may fall within the scope of the present invention, a preferred embodiment/preferred embodiments of the invention will now be described, by way of example only, with reference to the accompanying drawings in which.

DETAILED DESCRIPTION

Figure 1:
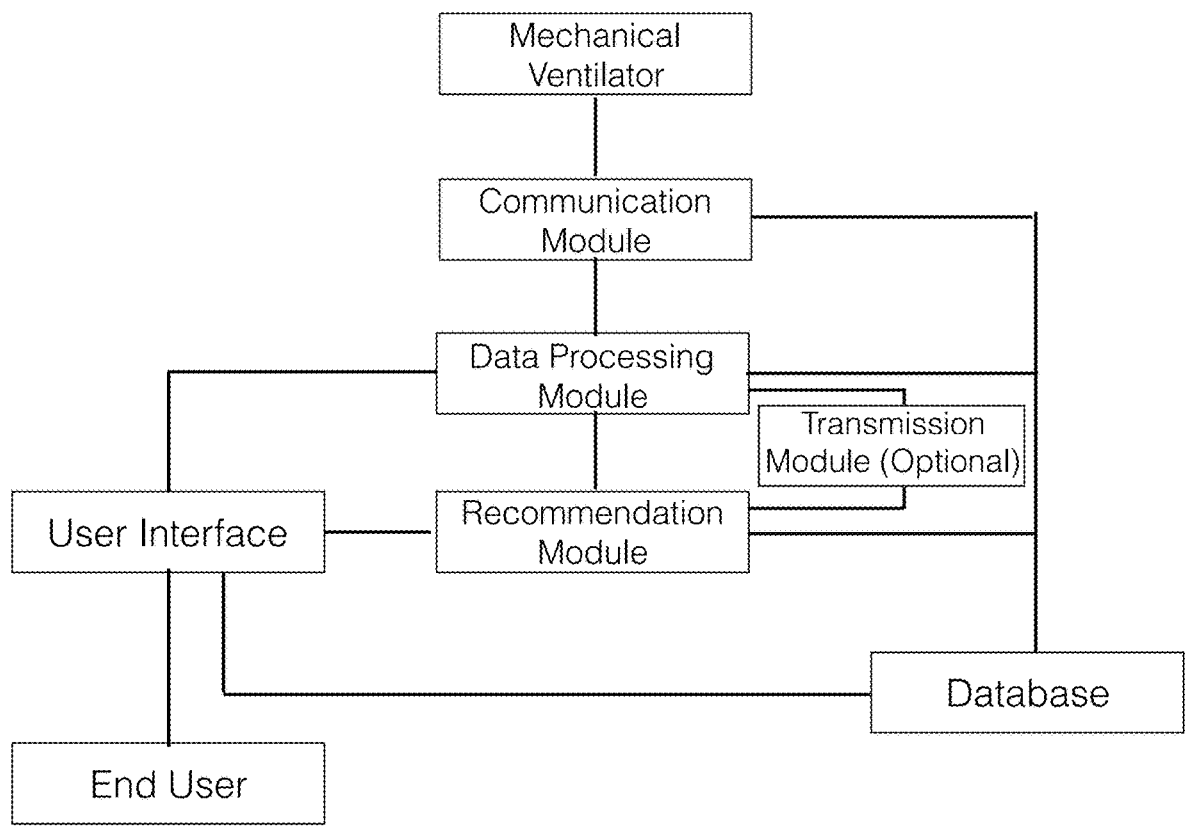
FIG. 1 is a schematic that illustrates the overall architecture of an embodiment of the clinical decision support system.

Respiratory failure can occur as a result of numerous factors, and patients in intensive care units (ICUs) are frequently placed on mechanical ventilators. Mechanical ventilation helps maintain lung function. Patient-ventilator asynchrony, also referred to as dyssynchrony, refers to a mismatch between ventilator delivery and patient demand. Patient-ventilator asynchrony can cause discomfort, and is associated with longer lengths of stay in ICUs. To address patient-ventilator asynchrony, clinicians can adjust ventilator settings or ventilation modes, change a patient's sedation level, or perform other interventions. Asynchrony can be detected by continuous monitoring of patients and using waveforms generated by mechanical ventilators. However, continuous monitoring of mechanically ventilated patients by clinical staff is infeasible.

The detection of asynchrony and the type of asynchrony requires specific training and knowledge of waveform analysis. If patient-ventilator asynchrony can be reliably detected via an automated algorithm, then the patient-ventilator asynchrony information can be displayed to the end user or used within a clinical decision support system for respiration management or within a mechanical ventilator to improve the functioning of the mechanical ventilator (e.g., optimizing triggering and cycling timing). The present disclosure describes a system that can be used to detect asynchronies and trends in asynchrony automatically. The information obtained using methods of the present disclosure can be used to alert hospital staff to adjust ventilator settings to prevent severe asynchrony. Algorithms embedded in mechanical ventilators can use patient-ventilator asynchrony information to change internal settings automatically, optimize or improve ventilator performance (e.g., triggering and cycling timings), or identify other relevant parameters that affect ventilator function. The system monitoring the patient for detecting asynchrony can alert a clinician or send a notification to a clinician for intervention if the patient is experiencing severe asynchrony.

Any algorithm described herein can be embodied in software or set of computer-executable instructions capable of being run on a computing device or devices. The computing device or devices can include one or more processor (CPU) and a computer memory. The computer memory can be or include a non-transitory computer storage media such as RAM which stores the set of computer-executable (also known herein as computer readable) instructions (software) for instructing the processor(s) to carry out any of the algorithms, methods, or routines described in this disclosure. As used in the context of this disclosure, a non-transitory computer-readable medium (or media) can include any kind of computer memory, including magnetic storage media, optical storage media, nonvolatile memory storage media, and volatile memory. Non-limiting examples of non-transitory computer-readable storage media include floppy disks, magnetic tape, conventional hard disks, CD-ROM, DVD-ROM, BLU-RAY, Flash ROM, memory cards, optical drives, solid state drives, flash drives, erasable programmable read only memory (EPROM), electrically erasable programmable read-only memory (EEPROM), non-volatile ROM, and RAM. The computer-readable instructions can be programmed in any suitable programming language, including JavaScript, C, C #, C++, Java, Python, Perl, Ruby, Swift, Visual Basic, and Objective C. Embodiments of the invention also include a non-transitory computer readable storage medium having any of the computer-executable instructions described herein.

A skilled artisan will further appreciate, in light of this disclosure, how the invention can be implemented, in addition to software and hardware, using one or more firmware. As such, embodiments of the invention can be implemented in a system which includes any combination of software, hardware, or firmware. In the context of this specification, the term "firmware" can include any software programmed onto the computing device, such as a device's nonvolatile memory. Thus, systems of the invention can also include, alternatively or in addition to the computer-executable instructions, various firmware modules configured to perform the algorithms of the invention.

According to embodiments, the computing device or devices can include a mainframe computer, web server, database server, desktop computer, laptop, tablet, netbook, notebook, personal digital assistant (PDA), gaming console, e-reader, smartphone, or smartwatch, which may include features such as a processor, memory, hard drive, graphics processing unit (GPU), and input/output devices such as display, keyboard, and mouse or trackpad (depending on the device). Embodiments can also provide a graphical user interface made available on one or more client computers. The graphical user interface can allow a user on a client computer remote access to the method or algorithm.

Additional embodiments of the invention can include a networked computer system for carrying out one or more methods of the invention. The computer system can include one or more computing devices which can include a processor for executing computer-executable instructions, one or more databases, a user interface, and a set of instructions (e.g., software) for carrying out one or more methods of the invention. According to other embodiments, the computing device or devices can be connected to a network through any suitable network protocol such as IP, TCP/IP, UDP, or ICMP, such as in a client-server configuration and one or more database servers. The network can use any suitable network protocol and can be any suitable wired or wireless network including any local area network, wide area network, Internet network, telecommunications network, Wi-Fi enabled network, or Bluetooth enabled network.

Patient-Ventilator Asynchrony Types

The primary types (categories) of patient-ventilator asynchrony include double triggering, ineffective triggering, premature termination, delayed termination, and flow starvation (i.e., excessive respiratory muscle activity during inspiration for example due to inadequate flow or volume). Another asynchrony-related event includes evidence of air trapping. Evidence of secretions (i.e., fluid build-up in the lungs and ventilator circuit) or fluid in the ventilator circuit can be detected using waveforms. The disclosed clinical decision support system can notify clinicians to consider performing suction on a patient when secretions are detected. When neither premature termination nor delayed termination are used to classify a breath cycle, no cycling asynchrony can be used as the patient-ventilator asynchrony type. Furthermore, if no asynchrony is detected in a breath cycle, the breath's asynchrony type is "no asynchrony".

Delayed Termination—Delayed termination occurs when the end of mechanical inspiration exceeds a patient's neural inspiration—the expiratory valve opens after the patient has already initiated exhalation. A consequence of delayed termination is air trapping and ineffective triggering as a result of insufficient expiratory time and excessive tidal volume.

Premature Termination—Premature termination occurs when the end of mechanical inspiration precedes the end of a patient's neural inspiration—the expiratory valve prematurely opens before the patient stops inhaling. Premature termination subjects a patient to an increased risk of double triggering. When shortened expiration results in a double trigger, air trapping and auto-PEEP can occur, and can inhibit a patient from reaching subsequent trigger thresholds.

Ineffective Triggering—Ineffective triggers occur when patient inspiration occurs during mechanical expiration, when a patient is trying to inspire and trigger another breath towards the end of the mechanical expiration phase but the ventilator does not deliver support for those patient triggering efforts.

Inadequate Support—In certain scenarios including inadequate delivery of flow or volume (also referred to as flow starvation or air hunger in volume control ventilation), i.e., when a patient desires more air than what is delivered by the ventilator during inspiration, a patient excessively engages the respiratory muscles during inspiration. Similarly, excessive respiratory muscle activity during inspiration can occur due to inadequate pressure support in the pressure control ventilation or pressure support ventilation modes. Finally, the patient may attempt to initiate a new breath by engaging the respiratory muscles during inspiration, which is referred to as ineffective effort during inspiration.

Double Triggering—Double triggering is the delivery of a second breath when the previous breath has not fully completed its inspiratory (inhalation) and expiratory (exhalation) phases. Double triggering involves a patient receiving a breath with an expiratory time less than one half of the mean inspiratory time or when the duration of expiration is less than a defined threshold (e.g., 500 msec). Double triggering may result in accumulation of air in the lungs (air trapping) such that the volume of air in the lungs at the end of the breath is greater than that at the start of the breath. Double triggering is a very serious asynchrony and can lead to barotrauma, where the lungs become hyperinflated.

Air Trapping—Air trapping occurs when a volume of inspired air is expired incompletely.

Aborted Breath—A breath is referred to as an aborted breath if the maximum tidal volume of a breath is less than a defined threshold (e.g., ½ of set tidal volume). An aborted breath can cause a patient to reject a breath delivered by the ventilator.

Irregular Breath—A breath is referred to as irregular if the shape of the waveform is substantially different from the pressure and flow waveform of a normal breath or a breath with asynchrony types discussed above. Breaths with substantially different shapes, where a reliable analysis of the breath is not possible, are considered irregular breaths.

No Asynchrony—If no asynchrony is detected in a breath cycle, the breath's asynchrony type is "no asynchrony" or "normal".

Overall Architecture of the Clinical Decision Support System

The present disclosure describes a system for detecting patient-ventilator asynchrony. In one embodiment, this clinical decision support system comprises the following components:

1. Communication Module—The Communication Module continuously downloads waveform and other data, such as settings and alarms, from a data source (e.g., mechanical ventilator, patient monitor) using an available communications port on the data source. If the patient-ventilator asynchrony detection system is implemented on a ventilator, the Communication Module continuously downloads waveform and other data from the appropriate internal component of the ventilator.

2. Data Processing Module—The Data Processing Module analyzes waveforms and other available data to detect patient-ventilator asynchrony events and asynchrony types. This comprises the steps of generating patient-ventilator interaction indicator waveforms, extracting features from the indicator waveforms, and classifying each individual breath cycle into categories of patient-ventilator asynchrony.

3. Data Logging Module—The Data Logging Module saves waveform, other extracted information, and the results of the analysis in a database.

4. Recommendation Module—The Recommendation Module uses detected asynchrony events, asynchrony types, and other detected events (e.g., detection of secretions or fluid in the circuit, or evidence of air trapping) to provide recommendations to an end user.

5. User Interface—The User Interface provides visualization of detected events and trends, and provides recommendations from the Recommendation Module to the end user. The end user can also review past waveforms to verify detected events by the system.

6. Transmission (Optional)—A transmission module is responsible for transmitting detected events and asynchrony information to a remote location (e.g., a remote server, a router, or a smartphone or tablet). A notification can alert clinicians to assess a patient experiencing asynchrony and make an appropriate action.

FIG. 1 illustrates the overall architecture of exemplary embodiments of the clinical decision support system.

Detection of Patient-Ventilator Asynchrony and Secretions Using Waveforms

The present disclosure describes a framework that uses pressure, flow, and volume waveforms to detect patient-ventilator asynchrony and the presence of secretions or fluid in the ventilator circuit. In some embodiments, the framework described herein is non-invasive. In some embodiments, the framework descried herein uses waveforms available from any model of mechanical ventilator.

Patient-Ventilator Asynchrony Detection Algorithm

The framework described herein uses pressure and flow waveforms from a mechanical ventilator to detect asynchrony and other events, such as the presence of secretions or air trapping. The first step involves segmenting a continuous waveform to identify individual breath cycles. Breath cycles are then analyzed further using a series of classifiers and labeling algorithms.

The overall framework described herein comprises a cascade of classifiers and labeling algorithms, where a breath cycle is fed into a series of classifiers and labeling algorithms in sequence. In some embodiments, the classifiers or labeling algorithms are rule-based, i.e., if a certain condition holds, the breath is classified or labeled as a certain asynchrony/respiratory event. In some embodiments, the asynchrony or event under consideration is not present. In some embodiments, the classifiers or labeling algorithms use supervised learning classification algorithms, such as random forests or neural networks, where the parameters of the classifier model are identified beforehand through a training process. Classifiers (e.g., random forests, neural networks, or support vector machines) that belong to the class of supervised learning classifiers are referred to as statistical classifiers or machine learning classifiers. The classifiers are arranged in a sequential framework. In some embodiments, a breath cycle is assigned to an appropriate class if a certain asynchrony is detected. In some embodiments, a breath cycle is assigned to a class where the asynchrony under consideration is absent, and the next classifier in the chain is engaged to analyze the breath cycle.

An example of a framework described herein used to detect patient-ventilator asynchrony and other related events comprises the following steps:

1. Acquire waveform data, including at least the flow and pressure from the ventilator.
2. Perform breath cycle segmentation, where the continuous waveform is analyzed to find individual breath cycles (i.e., start of inspiration to end of expiration, or using data provided by a ventilator to detect the start and end of a breath).
3. Select a breath cycle in the queue of breath cycles to be analyzed.
4. Perform signal denoising and filtering on the waveforms of the selected breath cycle to remove artifacts.
5. If volume waveform is not available, generate the volume waveform from the flow waveform using cumulative integration over time.
6. If evidence of secretion exists, add the secretion label to the breath cycle.
7. Check whether the breath is considered an aborted breath. An aborted breath is a breath cycle where the total delivered volume of the breath is less than a specific threshold (e.g., <½ set tidal volume). If an aborted breath is detected, then classify the current breath cycle as an aborted breath and proceed to Step 3.
8. Check if the breath cycle satisfies the conditions of double triggering. If double triggering is detected, then classify the current breath as a double trigger and proceed to Step 3.
9. Check if the breath satisfies the conditions of air trapping. Air trapping is present if the value of the flow at end expiration is less than a defined negative number (e.g., −2 L/min) or if the difference between the inspired volume and expired volume is larger than a defined threshold (e.g., expired breath volume is less than 90% of inspired volume). If air trapping is detected, add the air trapping label.
10. Generate a newly-derived waveform (i.e., Delta waveform) from the normalized pressure and flow waveforms.
11. Extract features from the Delta waveform.
12. Check whether the breath is irregular. An irregular breath is a breath cycle with a waveform shape that is substantially different than a typical waveform (including normal and asynchronous breaths) or a breath with missing features on the Delta waveform. If an irregular breath is detected, then classify the current breath as irregular and proceed to Step 3.
13. Check for evidence of inadequate support during inspiration. If inadequate support is detected, add the inadequate support label.
14. Use features detected from the Delta waveform to detect if ineffective triggering exists. If ineffective triggering is detected, add an ineffective triggering label.
15. Use the extracted features from the Delta waveform as an input to a statistical (machine learning) classifier, and use the class assignment provided by the classifier to classify the breath into premature termination, delayed termination, or no cycling asynchrony categories.
16. If a breath is classified as a premature termination or a delayed termination, then go to Step 3.
17. If no label (e.g., air trapping, ineffective triggering, etc.) has been assigned to the breath, classify the breath to the "no-asynchrony" class. Otherwise, classify the breath to the "some form of asynchrony" class with an appropriate label.
18. Go to Step 3.

Figure 2:
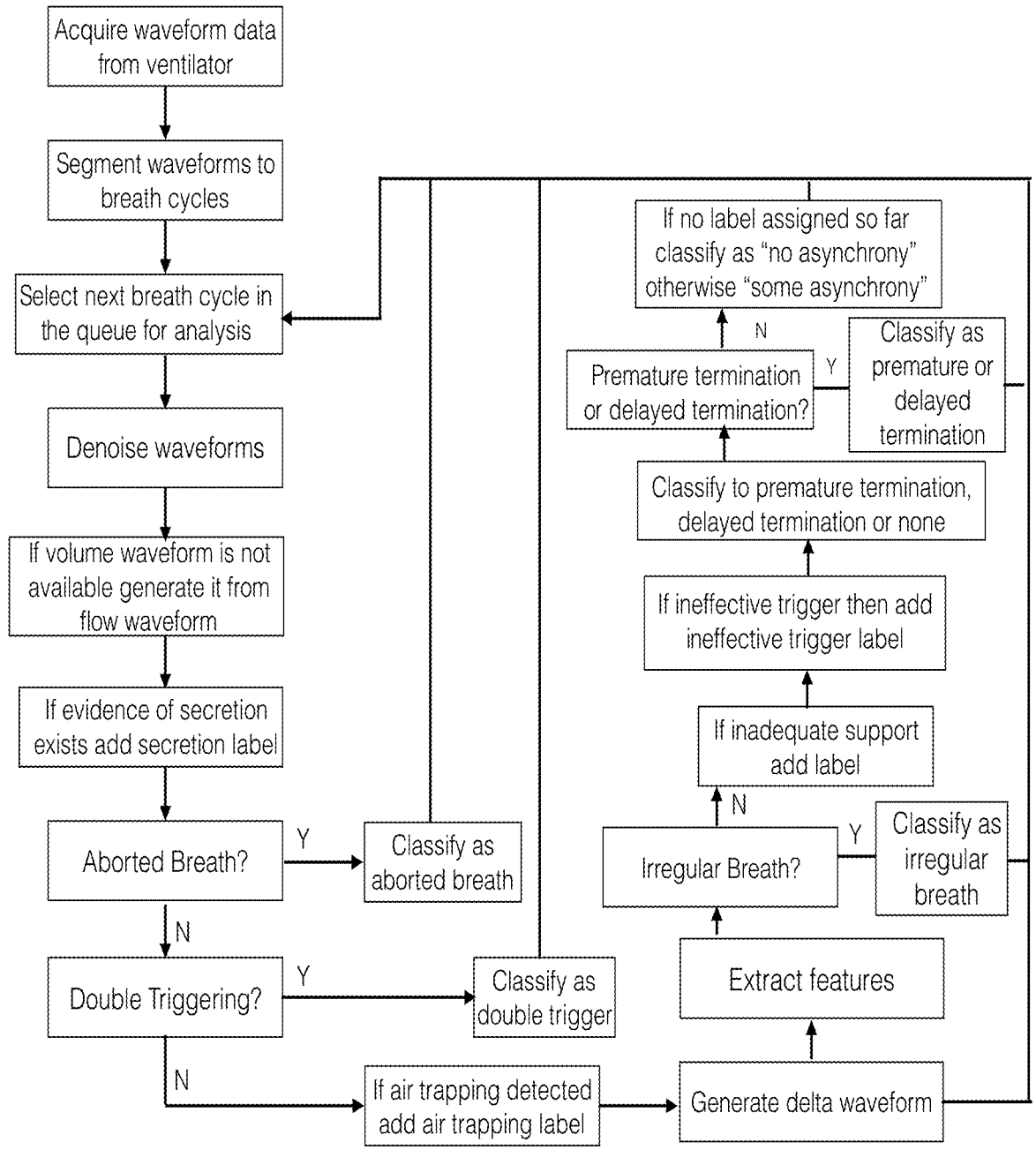
FIG. 2 is a flowchart that illustrates an embodiment of the components of the asynchrony detection algorithm.

FIG. 2 illustrates the steps discussed above in the form of a flow chart. In some embodiments, a breath can have a single label. In some embodiments, a breath can have multiple labels (e.g., secretion, air trapping, or inadequate support), and is assigned to one class.

Segmenting the Waveforms to Breath Cycles

Ventilators can provide the start and end times associated with a complete breath cycle. If the start and end times of a complete breath cycle are available, such data can be used to divide a continuous waveform into a series of breath cycles.

If a ventilator does not provide the start and end times associated with a complete breath cycle to segment waveforms into individual breath cycles, different techniques can be used to detect the start of a new breath. In some embodiments, the start of a new breath can be detected by identifying when air flow transitions from negative to positive (using an existing air flow sensor embedded in a ventilator) immediately prior to a peak positive flow.

Denoising Waveforms

Smoothing and filtering techniques can be used to remove noise and artifacts from pressure, flow, and volume signals. Denoising techniques used to remove noise and artifacts from pressure, flow, and volume signals include low pass filtering with finite impulse response (FIR), infinite impulse response (IIR) filters, wavelet denoising, and spline smoothing.

Generating Volume Waveform

If a volume waveform is unavailable from a mechanical ventilator, the volume waveform can be generated from the flow waveform for a specific breath cycle. In some embodiments, the flow waveform can be cumulatively integrated from the start to the end of a breath to generate a volume waveform.

Detecting Evidence of Secretions or Fluid in the Circuit

Figure 3:
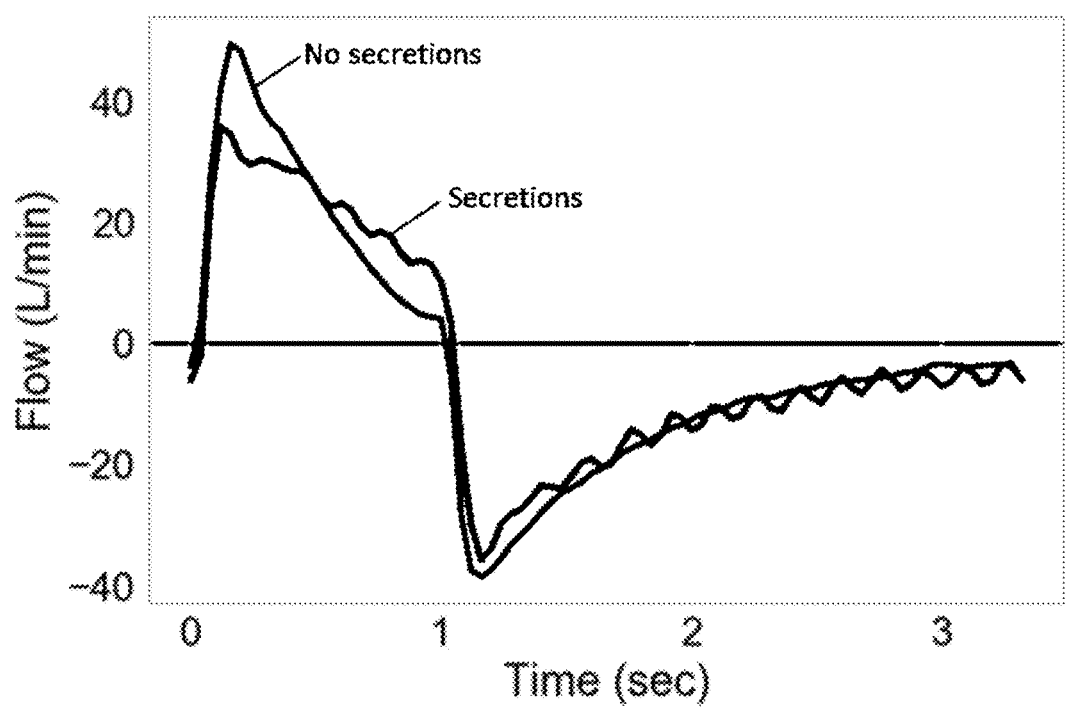
FIG. 3 is a waveform that depicts the flow waveform of breath showing evidence of secretions ('Secretions') compared to the flow waveform of a normal breath without evidence of secretions ('No secretions')

The presence of airway secretions or fluid in a ventilation circuit can produce saw tooth patterns on flow-volume loops. The oscillations are pronounced specifically on the flow waveform. FIG. 3 depicts the flow waveform of breath showing evidence of secretions or fluid in the ventilation circuit ('Secretions') compared to a normal breath without evidence of secretions ('No secretions').

Quantifying the amount of high frequency oscillations on flow waveforms can indicate the presence of secretions. The detection method must be robust to avoid false positives caused by other forms of oscillations on the flow waveform, such as cardiac oscillations. The automated detection of secretions or fluids in a circuit is important to minimize complications resulting from retained secretions and to prevent unnecessary suctioning.

To detect oscillations in the flow waveform that could indicate secretions, the present disclosure isolates high frequency oscillations in the flow signal, and measures the amplitude of the high frequency oscillations. In some embodiments, a seventh order IIR zero-phase high pass filter is used to extract oscillations above 5 Hz. To avoid including transient signals induced by opening and closing of ventilator circuits in the analysis, the middle 80% of expiration phase of the breath to high pass filter can be extracted and further analyzed.

A Hilbert transform can then be applied to obtain an envelope of the high frequency (e.g., >5 Hz) oscillations during exhalation. To assess the presence of secretions, the root-mean-square (RMS) value of the Hilbert transform can be calculated, where RMS of a time series (waveform) is defined as:

$$RMS = \sqrt{\frac{1}{n}\sum_{i=1}^{n} x_i^2}. \tag{1}$$

Figure 4:
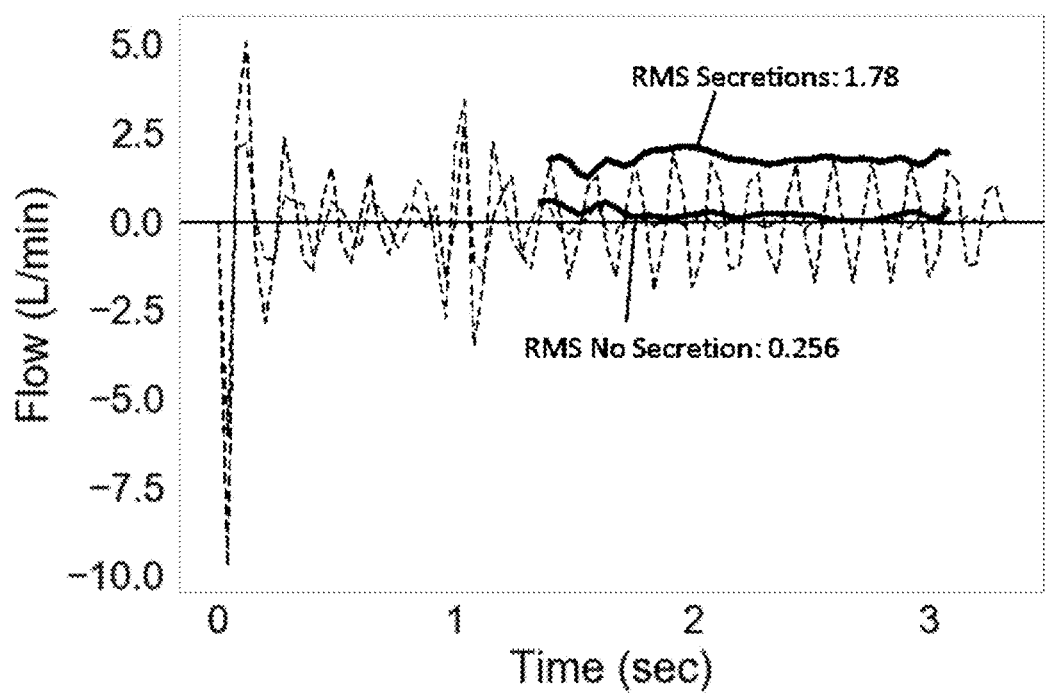
FIG. 4 is a graph that depicts the absolute value of the Hilbert transform of a segment of the expiratory phase of two breaths: breath with evidence of secretions ('Secretions') and breath without secretions ('No secretions')

If the RMS value is higher than a particular threshold (e.g., 1-2 L/min), a 'presence of secretion or fluid' label is assigned to the breath. FIG. 4 depicts the Hilbert transform of a segment of the expiratory phase of two breaths: with evidence of secretions ('Secretions') and without secretions ('No secretions'). The presence or absence of secretions or fluid in the circuit is independent of the presence of asynchrony. If secretions or fluids are detected, the algorithm can add a 'presence of secretion or fluid' label to the breath cycle. Whether a secretion label is assigned to a breath or not, the breath cycle is moved to the next step for further analysis.

Detecting Aborted Breaths

In some embodiments, a patient can abort or reject a breath. In some embodiments, aborted breaths are detected by low tidal volumes. In some embodiments, aborted breaths are detected using a rule-based technique: if the maximum delivered volume in the breath cycle is less than a particular threshold (e.g., one half of set tidal volume or mean tidal volume), then the breath is classified as an aborted breath and is removed from further analysis.

Detecting Double Triggering

To detect double triggering, the duration (or absence) of expiration must be detected. In some embodiments, double triggering is detected by analyzing the flow waveform of a breath. In some embodiments, the start of expiration of a breath can be determined by detecting the transition from positive to negative air flow. The absence of a transition from positive to negative air flow indicates an absence of expiration for a breath cycle. In some embodiments, the duration of expiration can be calculated as the duration of time that measured flow has the opposite sign (i.e., negative) as inspired flow.

When the duration of expiration, $T_{exp}$, is identified, then the inspiratory time $T_{insp}$ (i.e., duration of time from start of a breath to start of expiration) can be computed as the difference between breath cycle duration and $T_{exp}$. A rule-based technique can then be used to detect a double triggered breath when certain conditions are satisfied. In some embodiments, the rule used to detect double triggering is $T_{exp} < \frac{1}{2}$ mean $T_{insp}$. In some embodiments, the rule used to detect double triggering is $T_{exp} < \frac{1}{2}$ set $T_{insp}$. In some embodiments, the rule used to detect double triggering is $T_{exp}$ less than a defined threshold (e.g., 0.5 second). If a double triggering event is detected, that breath cycle is assigned to the double trigger class and removed from further analysis.

Detecting Air Trapping

In some embodiments, a rule-based technique is used to detect air trapping. In some embodiments, an air trapping label can be assigned to a breath if the value of flow at the end of expiration is less than a defined threshold (e.g., <−2 L/min). In some embodiments, an air trapping label is assigned to a breath if the expired volume is less than the inspired volume (e.g., expired volume is less than 90% of the inspired volume). If air trapping is detected, then an air trapping label is assigned to a breath. Whether an air trapping label is assigned to a breath or not, the breath is moved to the next step and further analyzed for other types of asynchronies.

Generating the Delta Waveform

A critical component of detecting patient-ventilator asynchrony is the extraction of features associated with various types of asynchrony. The present disclosure uses a newly defined waveform referred to as the Delta waveform to extract features associated with cycling asynchrony, ineffective triggering, and inadequate support. The definition of the Delta waveform as a means for indicating patient-ventilator interaction is independent of the mode of ventilation (e.g., pressure control ventilation, volume control ventilation, pressure support ventilation, etc.) and does not require a determination of when to deliver inspiration, expiration, or when to cycle between inspiration and expiration for its calculation.

The Delta waveform is defined as:

$$\delta(t) = \frac{p_{aw}(t) - p_e}{p_{aw}(t^*) - p_e} - \frac{q(t)}{q(t^*)}, \ t \geq t_0, \quad (2)$$

where t* represents the time of peak flow (i.e., $q(t) \leq q(t^*)$, $t \geq t_0$), and $p_e$ is the positive end expiratory pressure (PEEP). $p_{aw}$ is the airway pressure, q is the air flow, and to is the time at the start of the breath cycle. The Delta waveform represents the synchronized morphological difference between normalized pressure (after correcting for PEEP) and normalized flow waveforms. The operation of subtraction of constant $p_e$ and scaling by the constant $(p_{aw}(t^*) - p_e)$ to each data point in $p_{aw}$ represents the application of normalizing constants to the ventilator pressure waveform. Likewise, the scaling by the numerical constant $q(t^*)$ to each data point in q represents the application of normalizing constants to the ventilator flow waveform. The first term of Equation (2), $$\frac{p_{aw}(t) - p_e}{p_{aw}(t^*) - p_e},$$

is referred to as embodiment of a normalized ventilator pressure waveform. The second term of Equation (2), $$\frac{q(t)}{q(t^*)},$$

is referred to as an embodiment of a normalized ventilator flow waveform. In another embodiment of this second term of Equation (2), a constant $q_e$ can also be subtracted from both the numerator and denominator. In some embodiments, this constant $q_e$ can be the value of flow at end of exhalation (expiration) of the previous breath cycle. In another embodiment, the constant $q_e$ can be the initial value of the flow waveform. The resultant waveform calculated from Equation (2) is thus an embodiment of taking pairwise relationships between ventilator pressure and flow waveforms to generate a Delta waveform.

In other embodiments, normalization can be performed with respect to any time point within the inspiratory phase (mechanical inspiration). An inspiratory phase is defined as the interval of a breath cycle during which the ventilator is supplying inspiratory support or its inspiratory valves are open. An expiratory phase (mechanical expiration) is defined as the interval of a breath cycle during which the ventilator's expiratory valves are open thereby allowing the connected patient to exhale. In a first embodiment, normalization is performed with respect to t* (i.e., time of maximum flow) because t* can be robustly detected on the waveform. In other embodiments, Equation (2) can be modified to define a new Delta waveform by replacing t* with t, where t is any time point between to and the end of the inspiratory phase of the breath cycle. In a first embodiment, t can be the time elapsed into a breath cycle that is approximately the pressure rise time as set on the ventilator (i.e., time required for the ventilator-controlled pressure profile to reach a predetermined percentage of the set pressure support level). In a second embodiment, t can be the time elapsed into a breath cycle that is approximately the flow rise time as set on the ventilator (i.e., time required for the ventilator-controlled flow or volume profile to reach a predetermined percentage of the set peak flow or volume level).

In other embodiments, a suitable choice for t* can be informed by approximating the dynamics of the respiratory system with a first-order differential equation for airway pressure, $$p_{aw}(t) = R_{rs}\dot{V}(t) + \frac{1}{C_{rs}}V(t) - P_{mus}(t) + P_0,$$

where $R_{rs}$ is resistance of the respiratory system, $C_{rs}$ is compliance of the respiratory system, $p_{mus}$ is respiratory muscle pressure, $p_0$ is positive end-expiratory pressure (PEEP), V is volume, and $\dot{V}$ is air flow. Considering only the first two terms on the right-hand-side of the equation for $p_{aw}(t)$ representing the resistive and elastic forces, respectively, the resistive force contribution is maximized when V is at its maximum value and the elastic force contribution is minimal when V is at its minimum value. t* can be any suitable time point whereby $$R_{rs}\dot{V}(t^*) > \frac{1}{C_{rs}}V(t^*).$$

Without requiring knowledge of values for $R_{rs}$ and $C_{rs}$, t* can be chosen as a suitable time about the beginning of inspiratory phase whereby flow is close to its maximum value and volume is close to its minimum. Any equivalent criteria wherein choosing t* coincides with a suitable time point into mechanical inspiration wherein resistive forces of the patient-ventilator circuit dominate elastic forces can be used (e.g., multi-compartmental models of the respiratory system) without departing from the essence of the present disclosure.

The Delta waveform does not inform on when to deliver inspiration, expiration or when to cycle between inspiration and expiration. However, patterns of morphological features extracted from the Delta waveform can indicate when an already delivered breath by a ventilator was out of sync with patient respiratory efforts (i.e., patient-ventilator asynchrony event). The following section describes various Delta-waveform-specific features that can be extracted to classify breath cycles into categories of patient-ventilator asynchrony.

Feature Extraction from the Delta Waveform

The present disclosure can use a framework to extract a series of features from the Delta waveform that is used in the next steps of the algorithm for classification. The following definitions are used in the described framework.

Normalized pressure is defined as:

$$\bar{p}(t) = \frac{p_{aw}(t) - p_e}{p_{aw}(t^*) - p_e}, t \geq t_0, \quad (8)$$

where t* represents the time of maximum flow (i.e., $q(t) \leq q(t^*)$, $t \geq t_0$) and $p_e$ is the extrinsic positive end expiratory pressure. Normalized flow is defined as:

$$\bar{q}(t) = \frac{q(t)}{q(t^*)}, t \geq t_0. \quad (9)$$

Normalized pressure and flow in (8) and (9) can be similarly defined by replacing t* with t, where t is any time point between to and the end of the inspiratory phase of the breath cycle.

The present disclosure extracts the following features from the Delta waveform to identify potential patterns associated with asynchrony. The grouping together of one or more features (e.g., a set of features) extracted from a Delta waveform forms a feature vector for that breath cycle.

Figure 6:
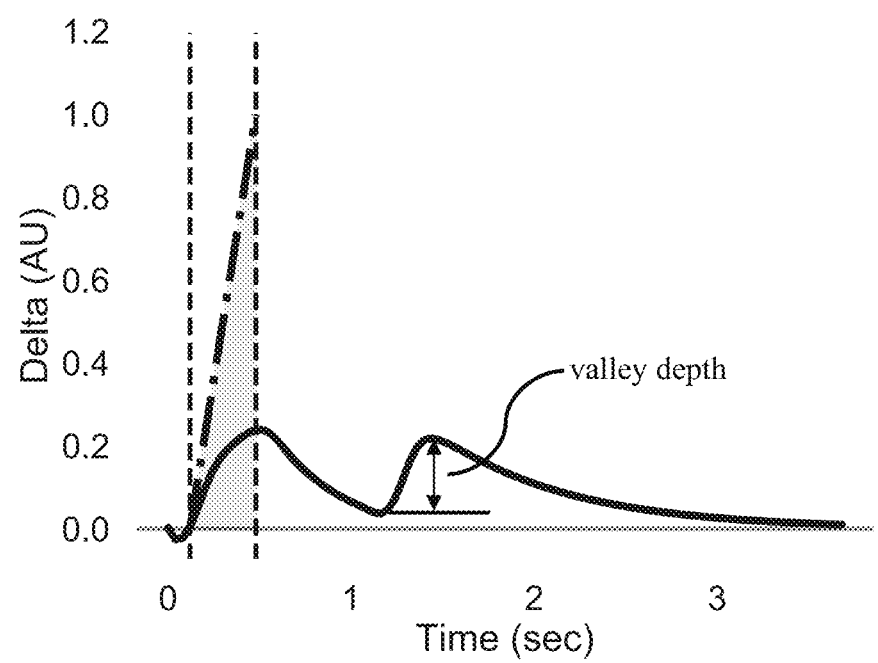
FIG. 6 is a graph that depicts an example of a patient-ventilator interaction indicating waveform ("Delta") of a sample breath cycle of premature termination asynchrony type.

Feature 1—Valley depth, defined as the difference between the value of the Delta waveform at a local minimum (valley) and a subsequent local maximum (peak), is chosen as a feature. FIG. 6 depicts the Delta waveform of a sample breath cycle involving premature termination that contains a single valley. There can be multiple valleys present in the Delta waveform, and for each valley the same definition of valley depth is used.

Feature 2—The second feature is defined as the maximum cross-correlation coefficient between the time derivative of the Delta waveform and the measured flow waveform. In an alternative embodiment, this feature can be defined as the maximum cross-correlation coefficient between the Delta waveform and the volume waveform (delivered tidal volume waveform) that is either calculated or received from a data source.

Feature 3—The third feature is the estimated inspiratory time $\hat{T}_{insp}$. In some embodiments, the estimated inspiratory time is defined as the duration of time during which the normalized pressure waveform is larger than a specific threshold $\varepsilon_1$ (e.g., $\varepsilon_1$=0.25 or 0.5). Specifically, $\hat{T}_{insp}=t_1-t_0$, where:

$$t_0 = \min\{t: \bar{p}(t) \geq \varepsilon_1\} \quad (10)$$

$$t_1 = \max\{t: \bar{p}(t) \geq \varepsilon_1\} \quad (11)$$

In another embodiment, time $\hat{T}_{insp}$ is defined as the moment at which the exhalation valve of the ventilator is opened following the inspiratory phase (inspiration phase) of ventilation.

Figure 7:
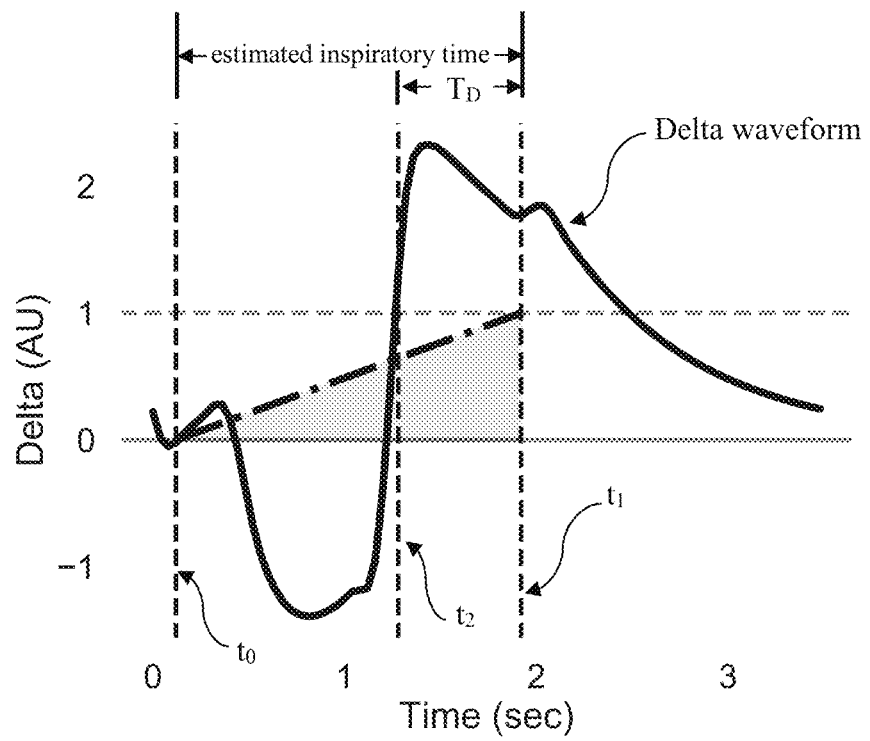
FIG. 7 is a graph that depicts an example of a patient-ventilator interaction indicating waveform ("Delta") of a sample breath cycle of delayed termination asynchrony type.
Figure 8A:
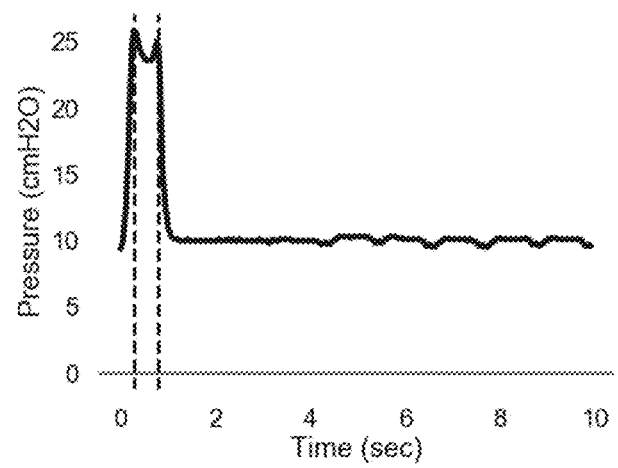
FIGS. 8A to 8C are waveforms that respectively depict an example of pressure (FIG. 8A), flow (FIG. 8B), Delta (FIG. 8C) waveforms for an ineffective triggering asynchrony type.
Figure 8B:
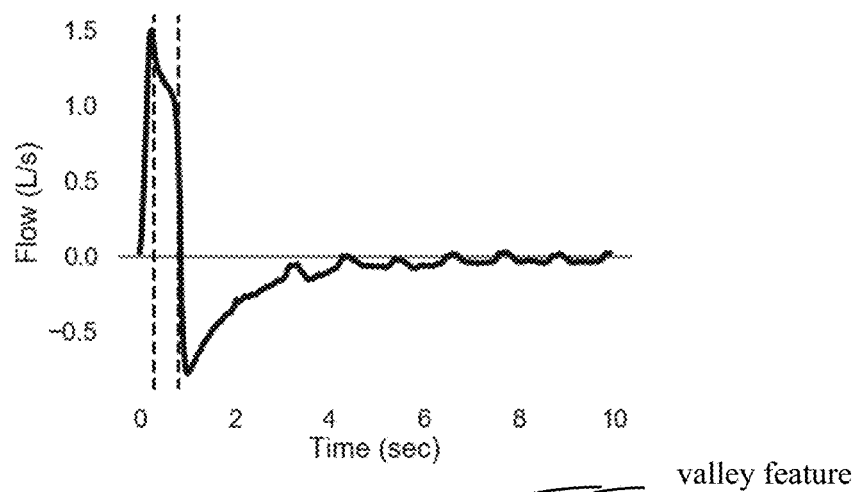
Figure 8C:
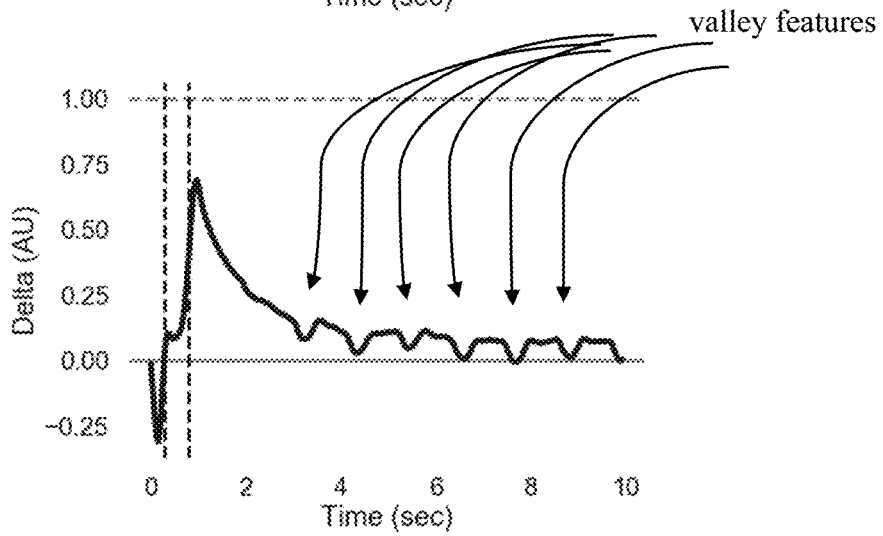

Feature 4—The ratio of area under the curve of the Delta waveform to area under the curve of a right triangle, $$\frac{A_1}{A_2},$$

is the fourth feature, where:

$$A_1 = \int_{t_0}^{t_1} \delta(t)dt, \quad (12)$$

$$A_2 = \frac{1}{2}\hat{T}_{insp}, \quad (13)$$

and $t_0$ and $t_1$ are given by (10) and (11), respectively, to define the (mechanical) inspiration phase of the breath cycle. FIG. 7 depicts the Delta waveform of a sample breath cycle involving delayed termination. $A_2$ is shown as the shaded triangular region in FIG. 7.

Feature 5—The ratio $$\frac{T_D}{\hat{T}_{insp}}$$

is the fifth feature as shown in FIG. 7, where $T_D = t_1 - t_2$, and $$t_2 = \min\{t: \delta(t) \geq 1\}. \quad (14)$$

Feature 6—The ratio $$\frac{T_{negative}}{\hat{T}_{insp}}$$

is the sixth feature, where:

$$T_{negative} = \int_{t_0}^{t_1} \mathbb{1}_f(\dot{V}(t) - \varepsilon_2)dt, \quad (15)$$

$\varepsilon_2$ is some threshold (e.g., $\varepsilon_2 = -2$ L/min), and $$f(x) = \begin{cases} 1, & x > 0, \\ 0, & x \leq 0. \end{cases} \quad (16)$$

Feature 7—The location of valley(s) detected in Feature 1 is selected as Feature 7. In some embodiments, the absolute time from the start of the breath in seconds is used to quantify the location of the valley. In other embodiments, the location of the valley is quantified as a fraction of the length into a breath at which the valley occurs. In another embodiment, the location of the valley is quantified as a fraction of the length of inspiration. In other embodiments, the location of the valley is measured from the start of expiration and is expressed as the fraction of a duration of an expiration.

Feature 8—The number of valleys detected in the Delta waveform.

Detecting Irregular Breaths

A breath cycle is classified as irregular if at least one of the features above is missing and cannot be determined. In addition, if all features can be calculated but the value of one or more features falls outside the range of typical values for such features (e.g., if the difference between the observed value and the average value of a feature based on a labeled data set is larger than a threshold value), then the corresponding breath cycle is classified as an irregular breath.

In some embodiments, an irregular breath can be detected by defining a distance metric between breaths to measure the similarity between waveforms of breaths (e.g., flow waveform or pressure waveform). In some embodiments, the similarity metric is the cross-correlation between two time-series.

In order to assess if a breath is irregular, the distance between the breath cycle under consideration and a collection of previously recorded breaths that are not considered irregular is calculated (i.e., synthetic breath cycles generated through simulation and/or previously recorded breath cycles classified or labeled as involving an asynchrony event or normal breaths with no evidence of asynchrony). If the distance of the breath under consideration from each individual breath in the collection is more than a defined threshold, then the breath is classified as irregular.

Detecting Inadequate Support During Inspiration

To detect inadequate support during inspiration, Feature 1, Feature 2, and Feature 7 are used. In some embodiments, Feature 1 and Feature 7 are modified, and the detection of a local minimum (valley) of the Delta waveform is limited to the inspiratory phase. In some embodiments, Feature 2 is modified, and the maximum cross-correlation coefficient between the time derivative of the Delta waveform and the measured flow waveform in the inspiratory phase is calculated (or between the Delta waveform and calculated volume waveform in the inspiratory phase). In some embodiments, a rule-based algorithm is used; if the value of the features are above or below a defined threshold, an "inadequate support during inspiration label" is added to the breath. In some embodiments, a statistical classifier (e.g., random forest, support vector machine, or neural network) is used to detect the presence of inadequate support during inspiration. Whether inadequate support during inspiration label is assigned or not, the breath is moved to the next step and further analyzed for other types of asynchronies.

Detecting Ineffective Triggering

To detect ineffective triggering, Feature 1, Feature 2, and Feature 7 are used. In some embodiments, Feature 1 and Feature 7 are modified, and the detection of a local minimum (valley) of the Delta waveform is limited to the expiratory phase. In some embodiments, Feature 2 is modified, and the maximum cross-correlation coefficient between the time derivative of the Delta waveform and the measured flow waveform in the expiratory phase is calculated (or between the Delta waveform and calculated volume waveform in the inspiratory phase). In some embodiments, Feature 7 is defined as the location of the valley is measured from the start of expiration and expressed as a fraction of a duration of expiration.

In some embodiment, a rule-based algorithm is used, where if Feature 7 exceeds inspiratory time by a threshold and Feature 1 is larger than a threshold an "ineffective triggering label" is added. In some embodiments, a statistical classifier (e.g., random forest, support vector machine, or neural network) is used to detect ineffective triggering. Whether an ineffective triggering label is assigned or not, the breath is moved to the next step and further analyzed for other types of asynchronies.

Ineffective triggering is considered a label and not a class. Each breath cycle is assigned to one class, but can have multiple labels. In some embodiments, a breath cycle can include ineffective triggering and a second type of asynchrony (e.g., delayed termination). Thus, ineffective triggering is considered a label.

Detection of Premature Termination and Delayed Termination

Random forests classification is used to classify breaths into one of the following classes:

(i) premature termination;
(ii) delayed termination; and
(iii) no cycling asynchrony.

In some embodiments, other classifiers generally referred to as supervised learning classifiers such as support vector machines, Bayesian networks, or neural networks are used to classify breaths into one of the three classes described above. In random forests and other classification frameworks such as neural networks, a probability is assigned to each class label. The class label with the highest probability, or the class label with a probability higher than some threshold value, can be selected as the predicted class label. The probability associated with a class label can also be used as a measure of a classifier's confidence in assigning a breath to the specific class.

Using random forest or other classification frameworks, the classifier is trained on a training set of breath cycles, where each breath cycle is represented by extracted features discussed in Section 10 (Feature Extraction from the Delta Waveform) and ground truth class labels. In some embodiments, class labels can be provided by a clinician or a panel of clinicians, where pressure and flow waveforms are used for labeling or pressure and flow and other signals such as esophageal pressure or diaphragm activity are used for labeling. In some embodiments, synthetic pressure and flow waveforms can be generated based on different asynchrony scenarios and ground truth labels are known based on the synthetic scenario generated. In some embodiments, training data for training the machine learning classifier includes both labeled data from previously collected patient data and synthetic data. Once the classifier is trained on the training set and the internal parameters of the classifier (e.g., random forests) are determined, the classifier can be used to predict class labels for new breath cycles. If the breath is assigned to the premature termination or delayed termination class, then classification for this breath is complete. If the breath is classified as no cycling asynchrony, then the breath is moved to the next step and further analyzed for a final analysis.

Final Analysis

In the final stage, a breath cycle that has been classified as no cycling asynchrony and has no labels associated with inadequate support, air trapping or ineffective triggering is classified as "no asynchrony". A breath cycle that has been classified as no cycling asynchrony and has a label associated with inadequate support, air trapping and/or ineffective triggering is classified as "some form of asynchrony present" with an associated label (i.e., inadequate support, air trapping or ineffective triggering or a combination of these labels).

Notification and Recommendation Modules

Information on patient-ventilator asynchrony can be used within a clinical decision support system framework to display any detect asynchrony events. The clinical decision support system can also provide definitions for each asynchrony event and provide recommendations to the end-user to address detected asynchronies. In some embodiments, the end user is a respiratory therapist. In some embodiments, a fully automated mechanical ventilator can be used, and information on detected asynchronies can be sent to a mechanical ventilator's control unit to change ventilator settings or mechanical ventilation mode.

The recommendation module can be implemented as a rule-based expert system such that if the asynchrony index exceeds a certain threshold, the end-user is notified and depending on the type of asynchronies present one or more recommendations are provided to address the asynchrony. The asynchrony index is the fraction of breaths (including triggered and un-triggered attempted breaths) with one or more detected asynchronies over a period of time. In some embodiments, the asynchrony index is determined over a period time of about 15 seconds, 30 seconds, 1 minute, about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 3 hours, about 6 hours, about 12 hours, or about 24 hours.

Figure 23:
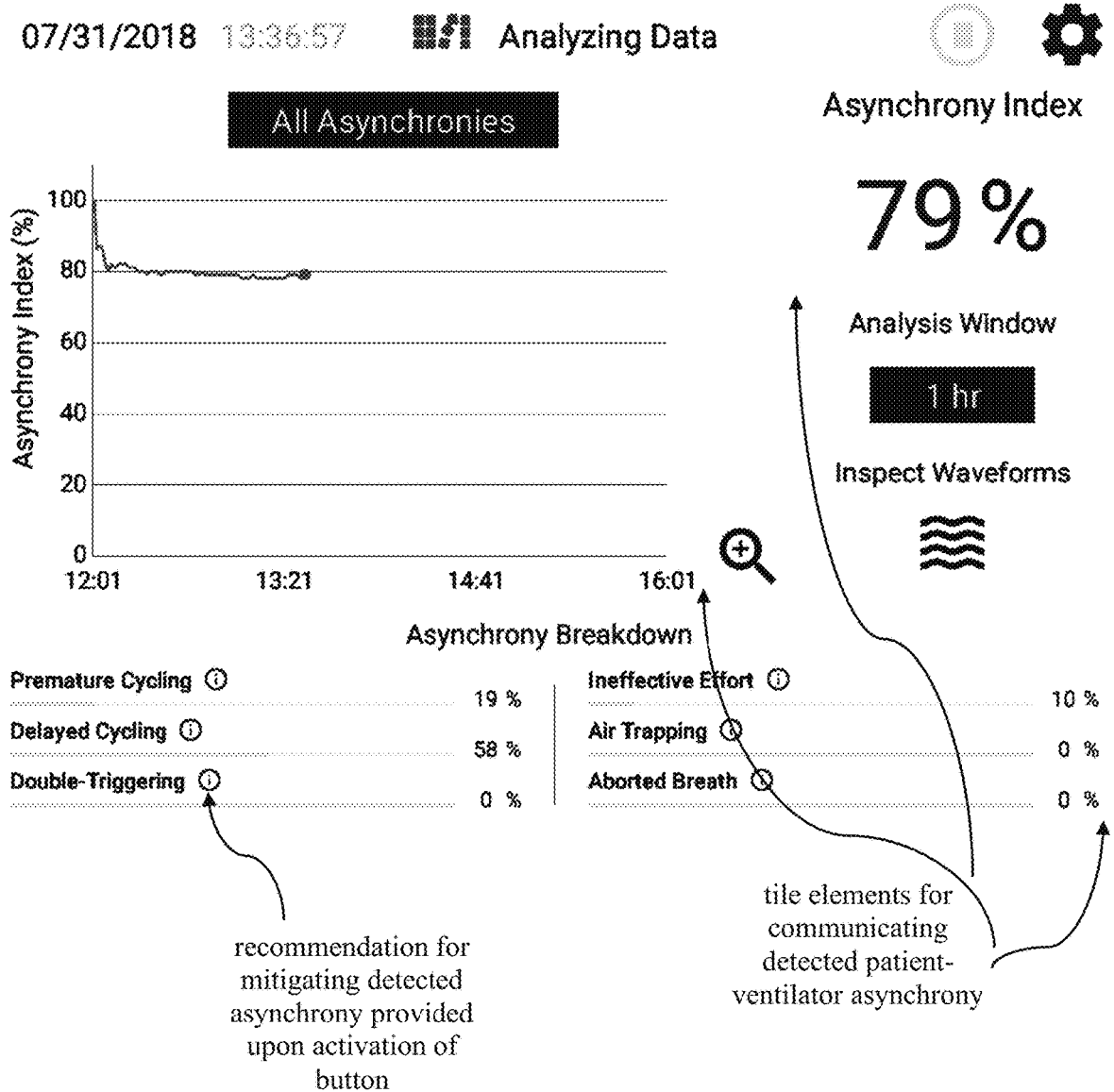
FIG. 23 is an illustration of an embodiment of a graphical user interface containing a window with elements communicating detected patient-ventilator asynchrony and recommendations for mitigating asynchrony.

In one embodiment of a system for detecting patient-ventilator asynchrony, a graphical user interface (GUI) is used for displaying prompts corresponding to detected patient-ventilator asynchrony, as shown in FIG. 23. In some embodiments, the GUI can display educational information on the detected asynchronies when a user taps on an information icon as shown in FIG. 23. In some embodiments, the GUI can display one or more recommendations for mitigating detected asynchronies when a user taps on an information icon as shown in FIG. 23.

Framework to Determine Parameters of Classification and Labeling Algorithms Using Synthetic Data Generated Using Simulation of Artificial Ventilation As discussed above, the classification and labeling of each breath cycle involves feeding the breath cycle to a series of classifiers and labeling algorithms. Classifiers and labeling algorithms can be either rule-based or based on a supervised learning machine learning algorithm (also referred to as a statistical classifier). In the rule-based algorithm, the value of one or more features extracted from waveforms are compared to one or more threshold values. In statistical classifiers, the classifier is first trained on a training set to identify the specific parameters of the classifier. Once the training is completed, the classifier uses the trained model to classify or label new breath cycles.

One drawback of determining optimal thresholds of a rule-based system or generating a large enough training set for a statistical classifier is that a data set from one or more patients is required. Furthermore, each breath in the data set requires a "ground truth" label or class corresponding to each asynchrony event. For example, to assign a label of class to each breath cycle, a common practice involves recording of esophageal pressure or electrical activity of the diaphragm to identify asynchrony events.

Alternatively, one may present the set of waveforms to a series of human expert to analyze each breath, one-by-one, to provide "ground truth" labels. In this disclosure, we present a framework to create "synthetic" waveform data using the model discussed below in Section Mathematical Modeling of the Respiratory System. Specifically, we can create a series of synthetic breaths under different conditions involving asynchrony or no asynchrony. Such data set can be used to determine the optimal value of thresholds for a rule-based algorithm or can be used as a training set for a statistical classifier. Since synthetic data is generated according to different known asynchrony scenarios, the ground truth labels for synthetic breaths are known. This framework presents a way to train rule-based and machine learning classifiers on waveform data and the corresponding ground truth label for each breath bypassing the need for manual labeling of breaths.

Mathematical Modeling of the Respiratory System

Dynamics of the respiratory system can be approximated by a first-order differential equation for a single-compartment lung model given by:

$$p_{aw}(t) = R_{rs}\dot{V}(t) + \frac{1}{C_{rs}}V(t) - p_{mus}(t) + p_0, \, t \geq t_0, \quad (17)$$

where $t_0$ is the start of the breath cycle, $$\dot{V}(t) = C_{rs}\frac{dp_c}{dt} \quad (18)$$

$R_{rs}$ is respiratory system resistance, $C_{rs}$ is respiratory system compliance, $\dot{V}(t)=q(t)$ is flow, $V(t)$ is respiratory system volume, $p_{mus}(t)$ is the amplitude of (negative) pressure generated by respiratory muscles, and $p_0$ is a constant. Pressure, flow, and volume relationships are assumed to be linear. Other substitutions can be made to the model without departing from the spirit of generating synthetic data for use in training a machine learning algorithm or tuning a classifier.

Figure 5:
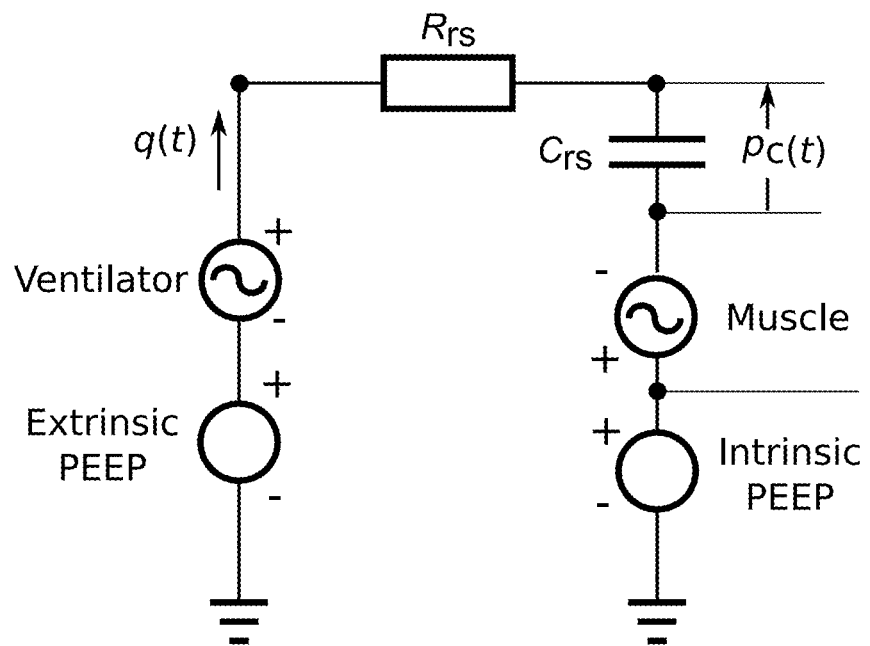
FIG. 5 is a schematic that illustrates an electrical analogue of the respiratory system.

The respiratory model in Equation (17) can be represented by an equivalent electrical analogue consisting of a series arrangement of: a) a resistor element with resistance $R_{rs}$ representing the resistance of the total respiratory system; and b) a capacitor element with capacitance $C_{rs}$ representing total compliance of the respiratory system. FIG. 5 illustrates an electrical analogue of the respiratory system. Constant $p_0$ of Equation (17) is the sum of Extrinsic PEEP and Intrinsic PEEP in the electrical analogue.

A time-varying source representing a mechanical ventilator for the inlet boundary condition is included in the electrical analogue and labeled as Ventilator to represent the presence of a mechanical ventilator. Depending on the mode of ventilation, an equivalent pressure (voltage) waveform or flow (current) waveform can be used to model the pressure and volume control ventilation modes, respectively. Constant sources are also added to model extrinsic PEEP $p_e$ and intrinsic PEEP $p_i$.

In another embodiment, $R_{rs}$ can be further modified to have different values during inspiration $R_{rs,insp}$, and during expiration, $R_{rs,exp}$. The governing equations for the model can then be split into inspiratory and expiratory phases:

$$p_{aw}(t) = R_{rs,insp} \dot{V}(t) + \frac{1}{C_{rs}} V(t) - p_{mus}(t) + p_0, t_0 \leq t \leq t_1, \quad (19)$$

$$p_{aw}(t) = R_{rs,exp} \dot{V}(t) + \frac{1}{C_{rs}} V(t) - p_{mus}(t) + p_0, t_1 < t \leq t_{breath}, \quad (20)$$

where the interval $t_0 \leq t \leq t_1$ represents the inspiratory phase, the interval $t_1 < t \leq t_{breath}$ represents the expiratory phase, and the breath cycle having a total duration of $t_{breath} - t_0$ seconds. In other embodiments, the single-compartment model can be extended to have more compartments by addition of resistive and capacitive elements to the electrical analogue without departing from the spirit of generating synthetic data for use in training a machine learning algorithm or tuning a classifier.

Creation of Synthetic Breaths and Feature Vectors

In one embodiment of creating a plurality of synthetic breaths (ventilator pressure and flow waveforms), the respiratory system is modeled using the single-compartment lung model discussed in Section Mathematical Modeling of the Respiratory System. In the case of modeling ventilation in pressure control mode, the ventilator inlet boundary condition can be a rectangular pressure waveform such as that shown in FIG. 12A, annotated as the inlet boundary condition. Alternatively, in the case of modeling volume control mode, the ventilator inlet boundary condition can be any typical pattern of flow used for ventilation such as descending ramp flow pattern shown in FIG. 10B, annotated as the inlet boundary condition. Whatever the mode of ventilation being modeled, the inlet boundary condition defines when the ventilator cycles from inspiration to expiration (i.e., cycling off time), such as those shown in FIG. 10B for volume control mode and FIG. 12A for pressure control mode.

Figure 9A:
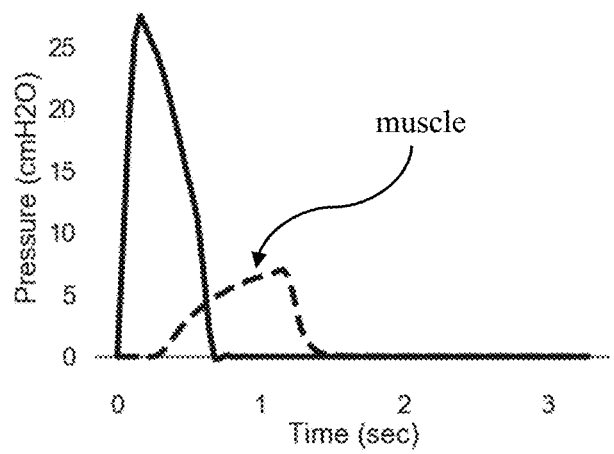
FIGS. 9A and 9B are waveforms that respectively depict an example of a synthetic set of pressure (FIG. 9A) and flow (FIG. 9B) waveforms for a premature termination asynchrony type in volume control ventilation mode.

In the case of modeling spontaneous efforts during mechanical ventilation, the pressure generated by the respiratory muscles can be any pulsatile pressure waveform typical of respiratory muscle effort. In some embodiments, an exponentially rising and decaying pulse as shown in the top panel of FIG. 9A, annotated as the muscle waveform, is used. A plurality of variations can be made to the inlet boundary conditions, such as to their shapes, timings, and durations, as well as to the muscle pressure profile, to produce a plurality of synthetic waveforms. The plurality of variations can further include variations in respiratory system resistance and compliance.

The respiratory system model can be implemented in vitro (e.g., a physical model employing elements such as actuators, valves, bellows, etc.) or in silico (e.g., a computational model simulated on a digital computer). In one embodiment of an in vitro representation, an electrical analogue of the respiratory system can be implemented directly with electrical circuit components (e.g., resistors, capacitors, voltage sources, current sources). In other embodiments, an in vitro representation can involve use of a breathing simulator attached to a mechanical ventilator. An embodiment of an in silico representation includes use of a digital computer to numerically solve the differential equations described in Section Mathematical Modeling of the Respiratory System. In some embodiments of an in silico representation, an electrical analogue model of the respiratory system can be solved with electronic circuit simulator design software. This may involve laying out each discrete electrical circuit element (e.g., resistors, capacitors, voltage sources, current sources) in a circuit schematic editor and using its supplied tools to simulate the model to output waveforms that approximate ventilator pressure (voltage waveforms) and flow waveforms (current waveforms).

Model parameters may be chosen based upon ranges in published literature or empirically varied to reproduce the ranges of waveforms encountered in clinical practice. Variations in parameters can also be used to generate varying degrees of patient-ventilator asynchrony. Since the specific clinical scenario for each in vitro or in silico simulation is known, the ground truth label for asynchrony type for the resulting breath cycle is known as well.

Figure 9B:
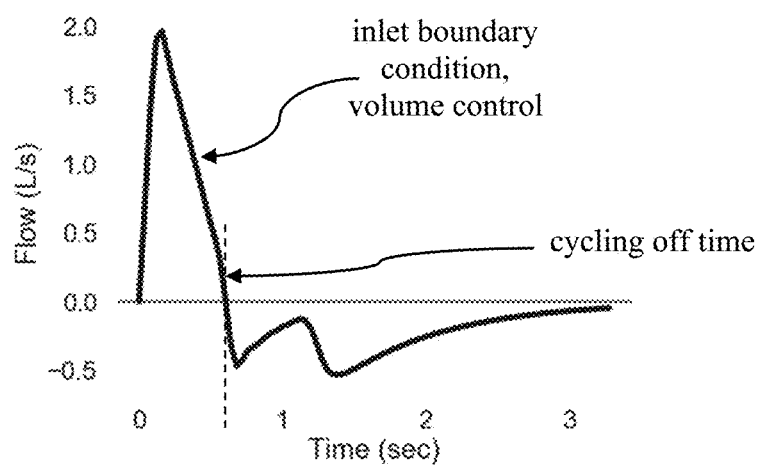
Figure 10A:
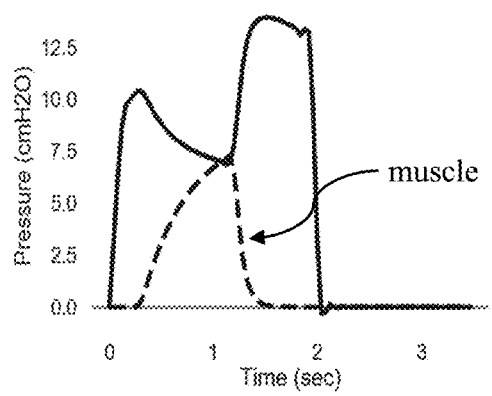
FIGS. 10A and 10B are waveforms that respectively depict an example of a synthetic set of pressure (FIG. 10A) and flow (FIG. 10B) waveforms for a delayed termination asynchrony type in volume control ventilation mode.
Figure 10B:
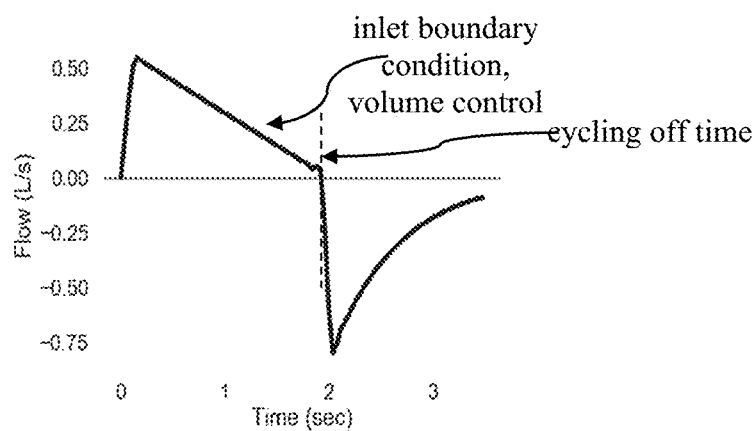
Figure 11A:
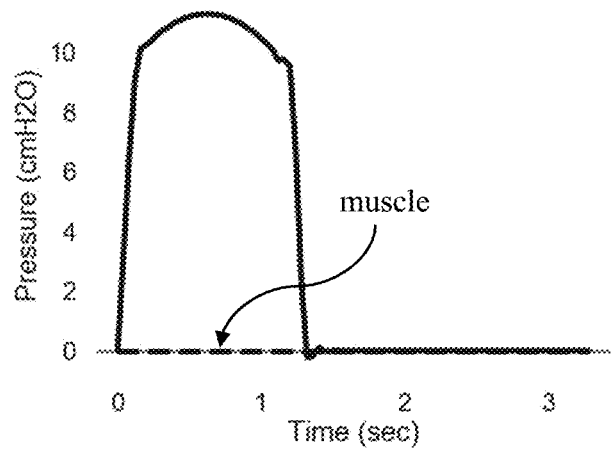
FIGS. 11A and 11B are waveforms that respectively depict an example of a synthetic set of pressure (FIG. 11A) and flow (FIG. 11B) waveforms for a passive patient with no spontaneous muscle activity in volume control ventilation mode.
Figure 11B:
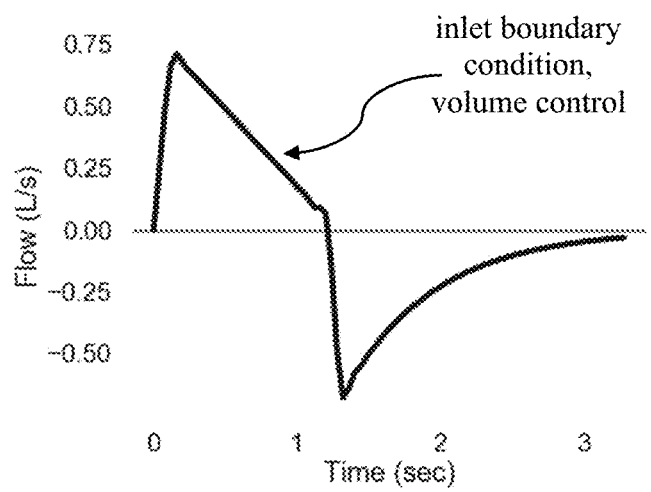
Figure 12A:
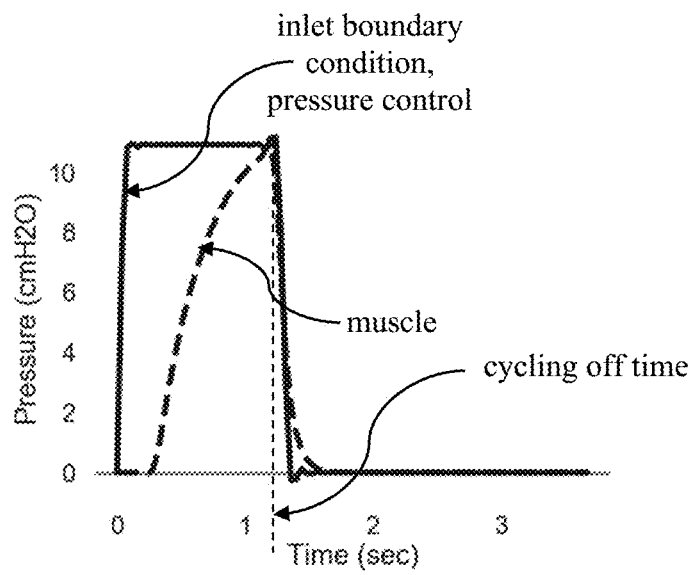
FIGS. 12A and 12B are waveforms that respectively depict an example of a synthetic set of pressure (FIG. 12A) and flow (FIG. 12B) waveforms for patient effort in sync with ventilator cycling in pressure control ventilation mode.
Figure 12B:
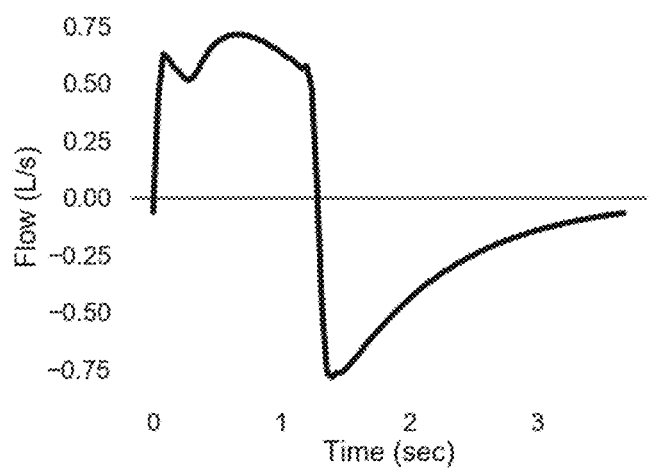
Figure 13A:
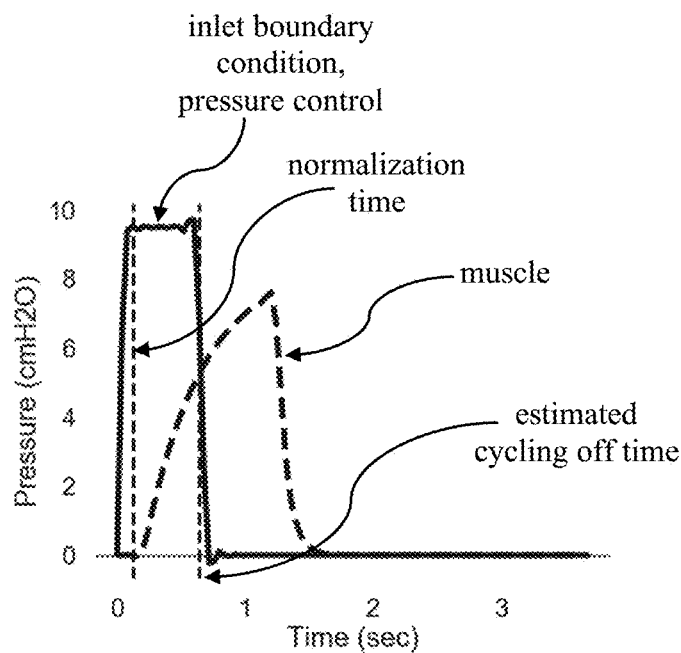
FIGS. 13A to 13C are waveforms that respectively depict an example set of pressure (FIG. 13A), flow (FIG. 13B) and Delta waveforms (FIG. 13C) for a premature termination asynchrony type in pressure control ventilation mode.
Figure 13B:
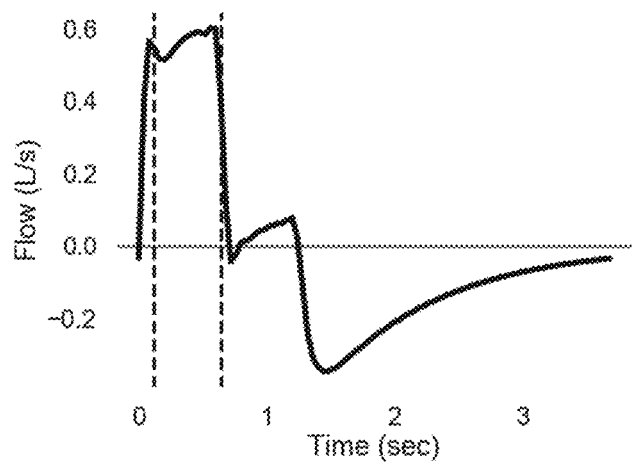
Figure 13C:
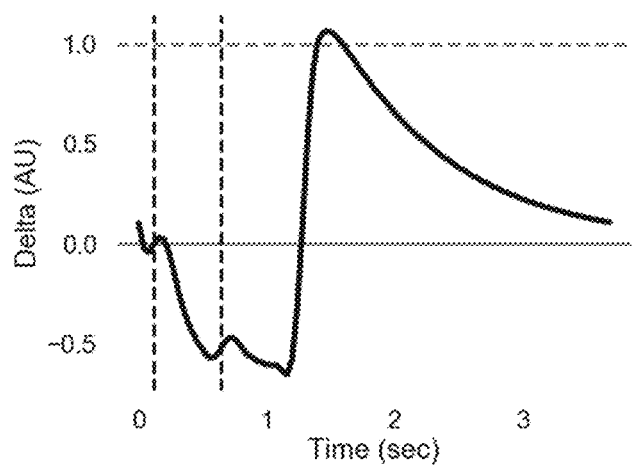
Figure 14A:
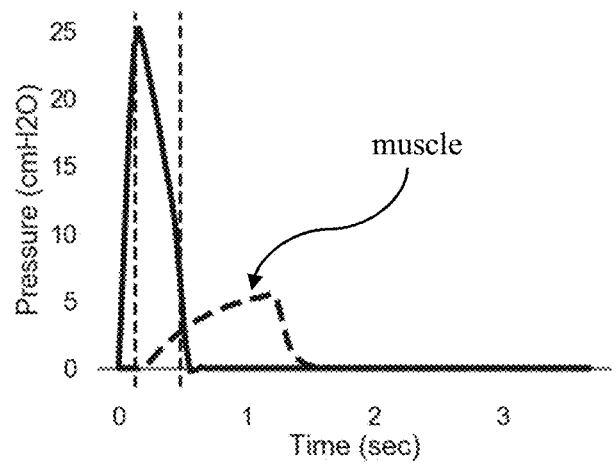
FIGS. 14A to 14C are waveforms that respectively depict an example set of pressure (FIG. 14A), flow (FIG. 14B) and Delta waveforms (FIG. 14C) for a premature termination asynchrony type in volume control ventilation mode.
Figure 14B:
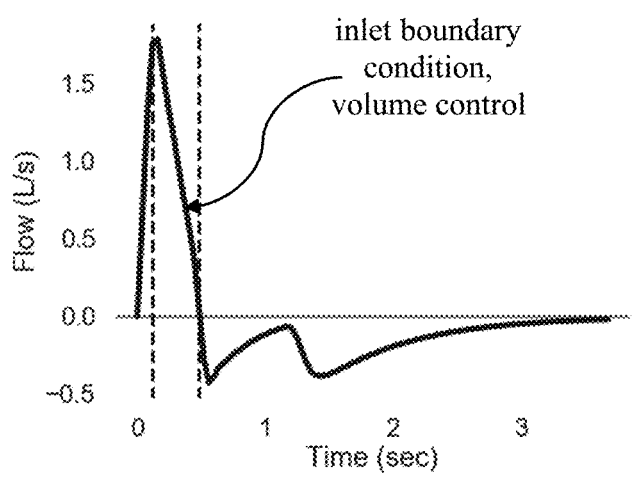
Figure 14C:
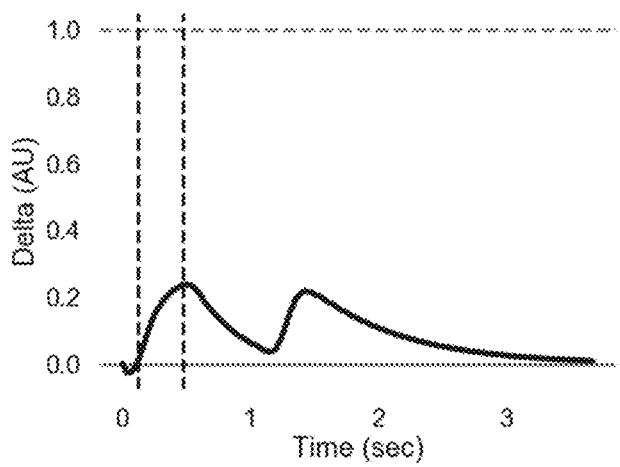
Figure 15A:
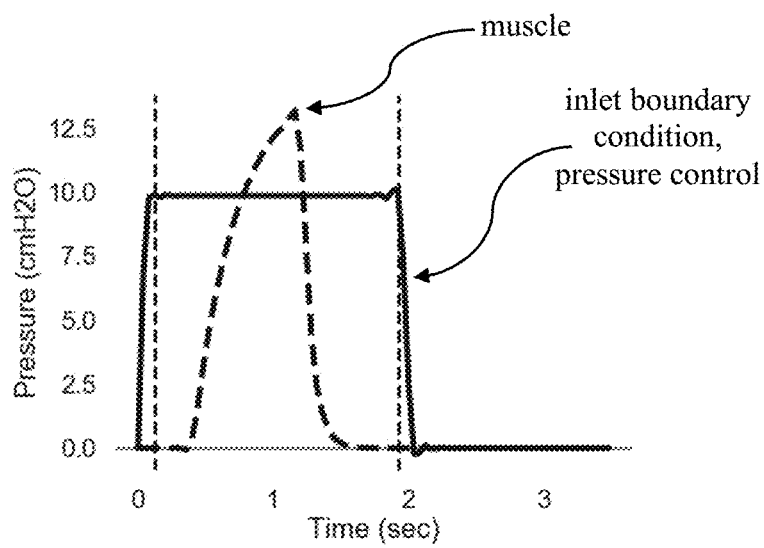
FIGS. 15A to 15C are waveforms that respectively depict an example set of pressure (FIG. 15A), flow (FIG. 15B) and Delta waveforms (FIG. 15C) for a delayed termination asynchrony type in pressure control ventilation mode.
Figure 15B:
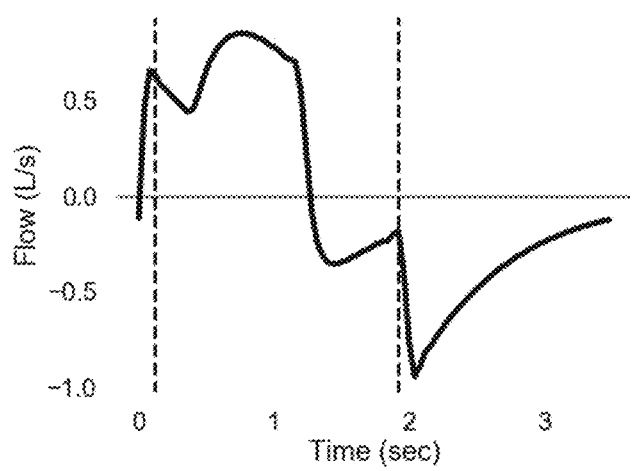
Figure 15C:
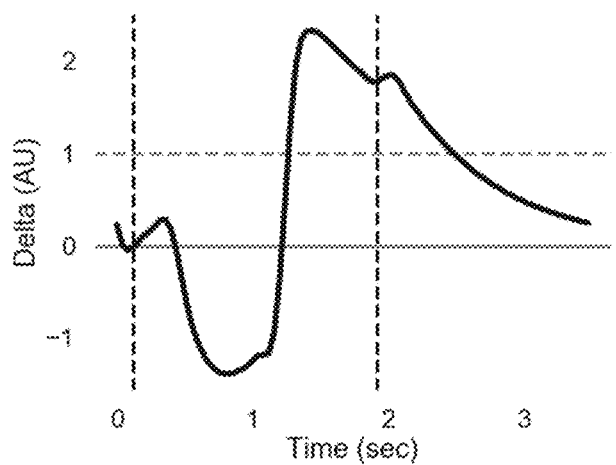
Figure 16A:
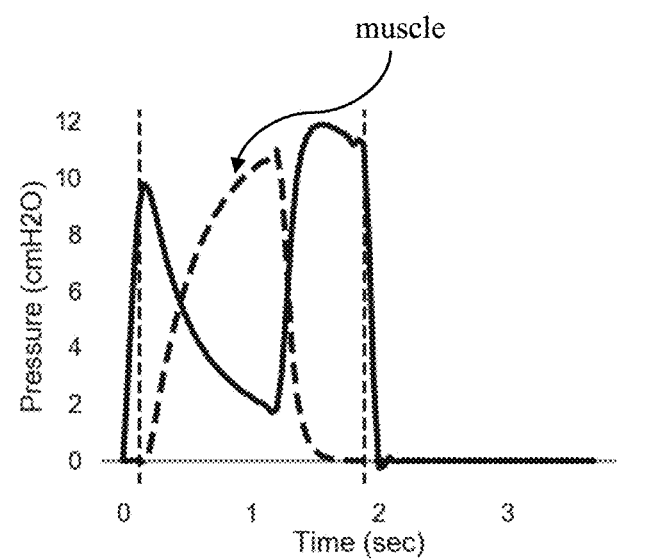
FIGS. 16A to 16C are waveforms that respectively depict an example set of pressure (FIG. 16A), flow (FIG. 16B) and Delta waveforms (FIG. 16C) for a delayed termination asynchrony type in volume control ventilation mode.
Figure 16B:
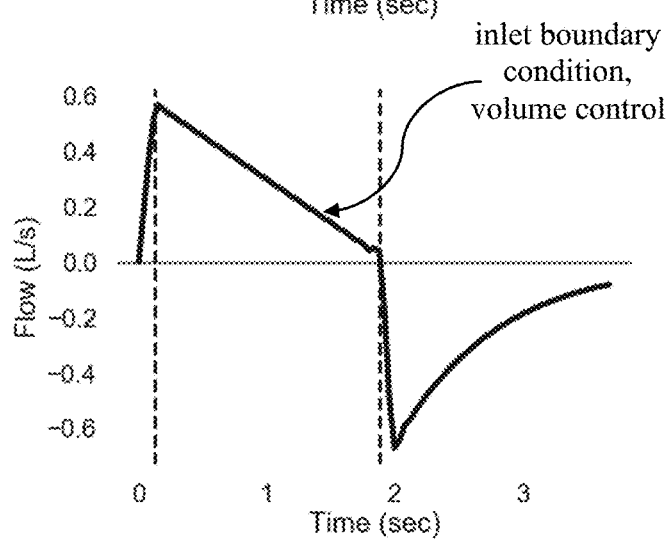
Figure 16C:
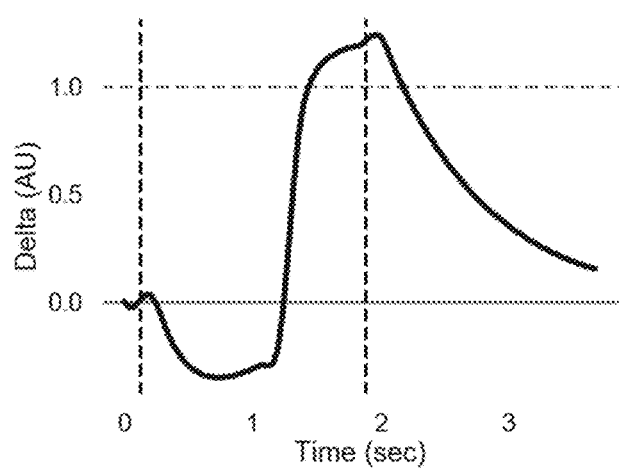
Figure 17A:
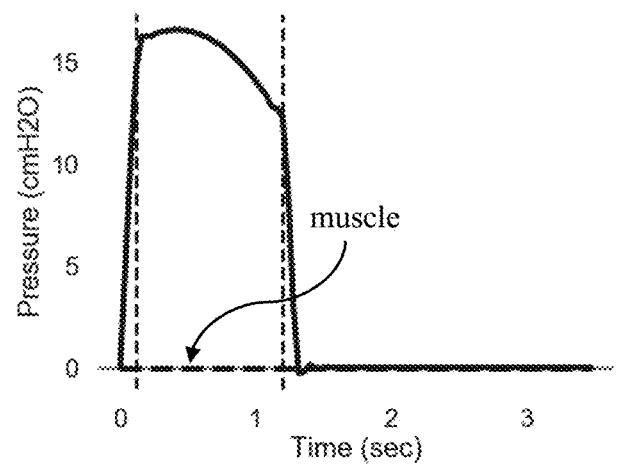
FIGS. 17A to 17C are waveforms that respectively depict an example set of pressure (FIG. 17A), flow (FIG. 17B) and Delta waveforms (FIG. 17C) for a passive patient in volume control ventilation mode.
Figure 17B:
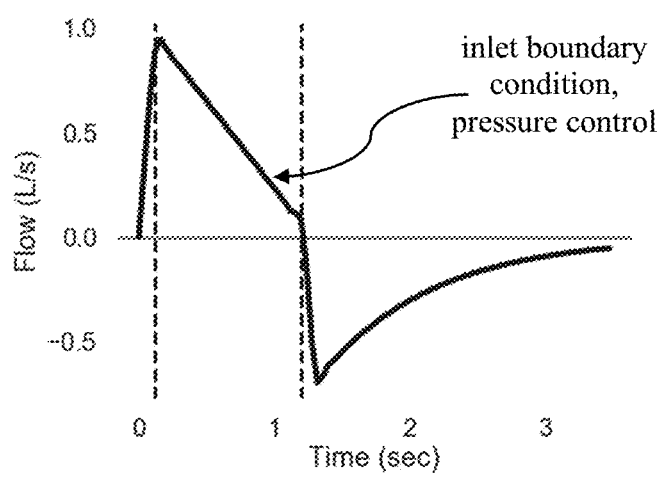
Figure 17C:
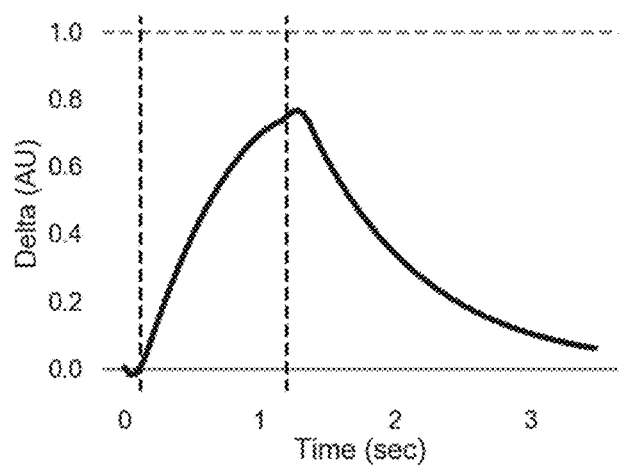
Figure 18A:
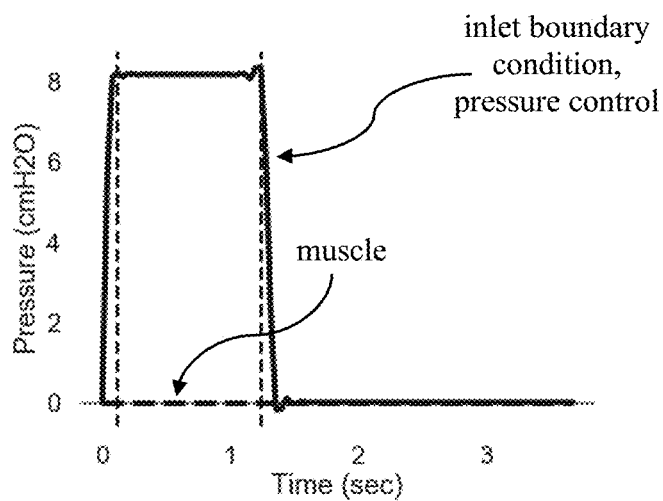
FIGS. 18A to 18C are waveforms that respectively depict an example set of pressure (FIG. 18A), flow (FIG. 18B) and Delta waveforms (FIG. 18C) for a passive patient in pressure control ventilation mode.
Figure 18B:
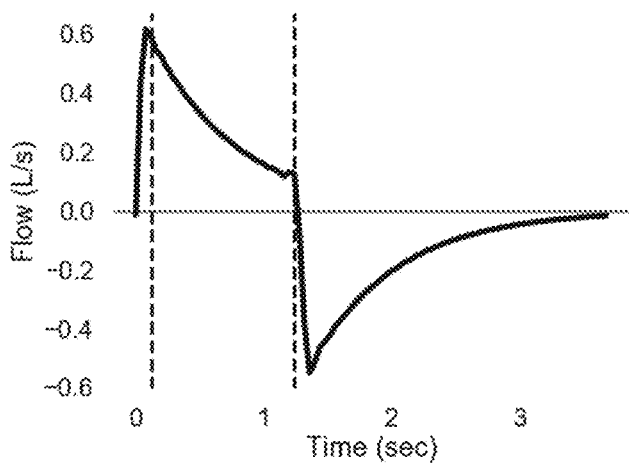
Figure 18C:
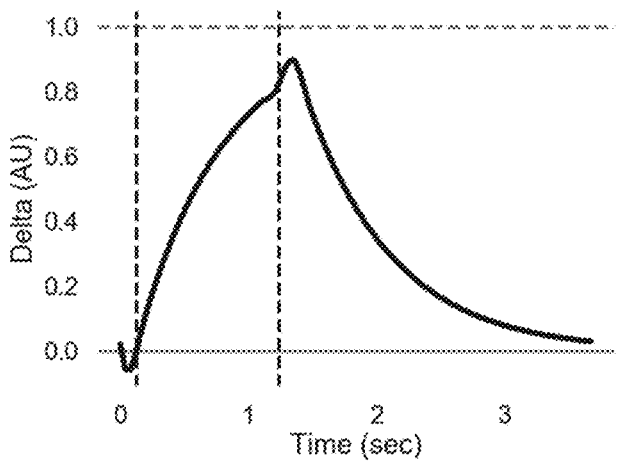
Figure 19A:
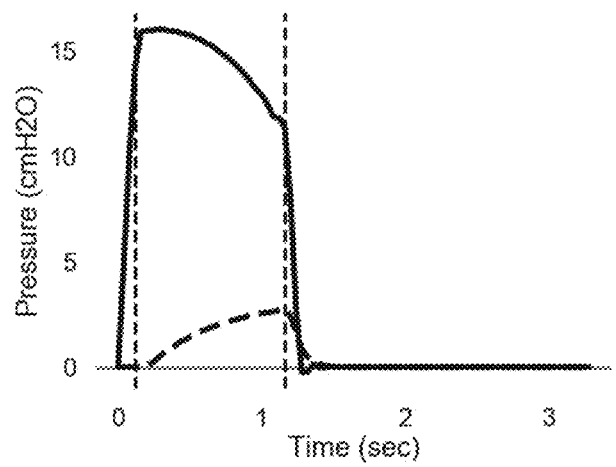
FIGS. 19A to 19C are waveforms that respectively depict an example set of pressure (FIG. 19A), flow (FIG. 19B) and Delta waveforms (FIG. 19C) for patient effort in sync with ventilator cycling in volume control ventilation mode.
Figure 19B:
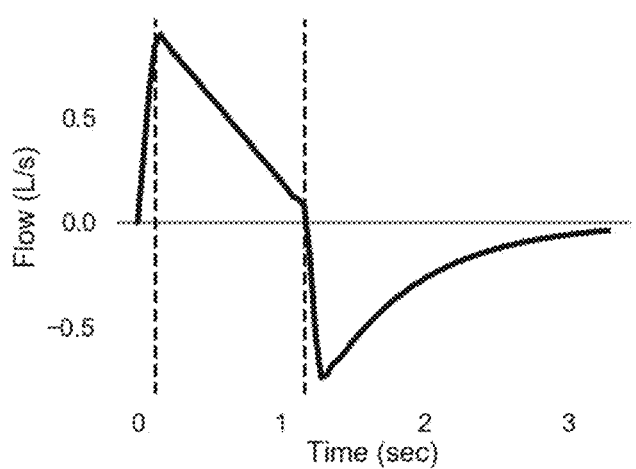
Figure 19C:
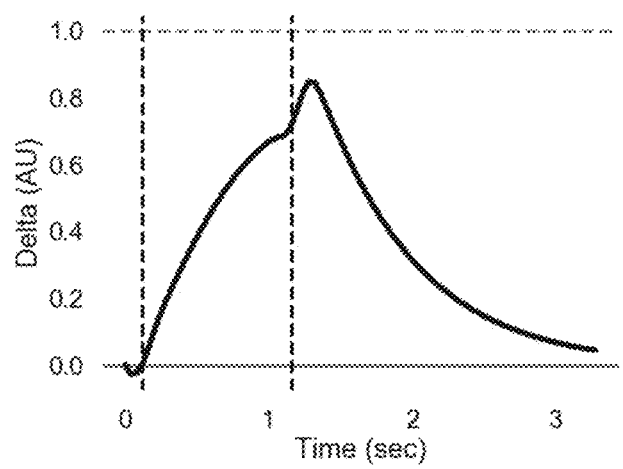
Figure 20A:
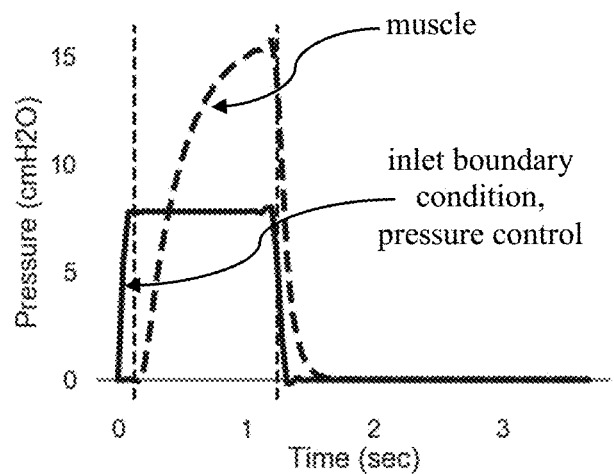
FIGS. 20A to 20C are waveforms that respectively depict an example set of pressure (FIG. 20A), flow (FIG. 20B) and Delta waveforms (FIG. 20C) for patient effort in sync with ventilator cycling in pressure control ventilation mode.
Figure 20B:
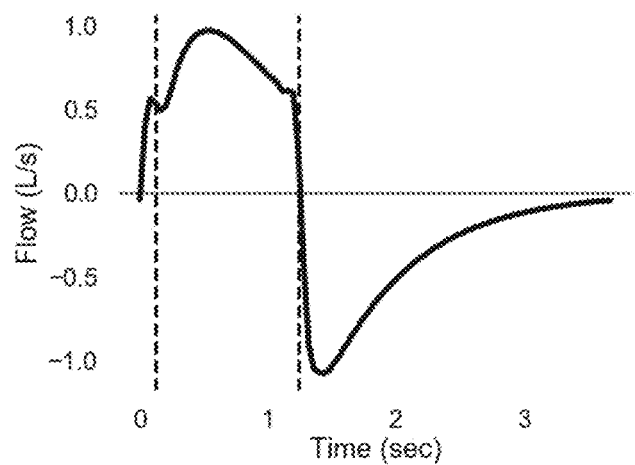
Figure 20C:
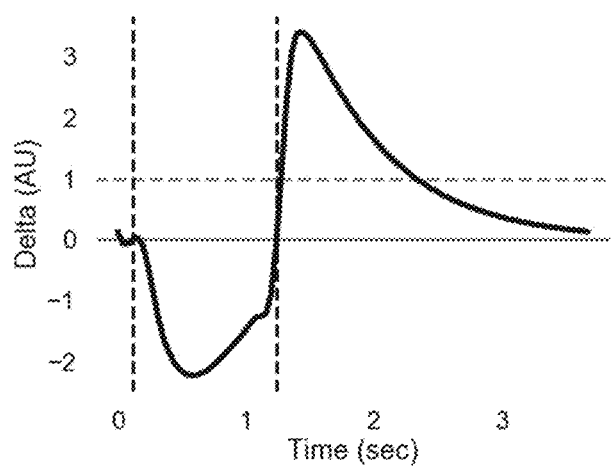
Figure 21A:
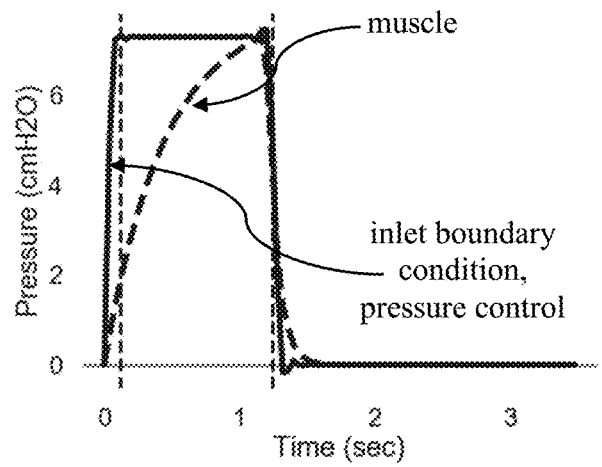
FIGS. 21A to 21C are waveforms that depict an example set of pressure (FIG. 21A), flow (FIG. 21B) and Delta waveforms (FIG. 21C) for patient effort in sync with ventilator cycling in pressure control ventilation mode.
Figure 21B:
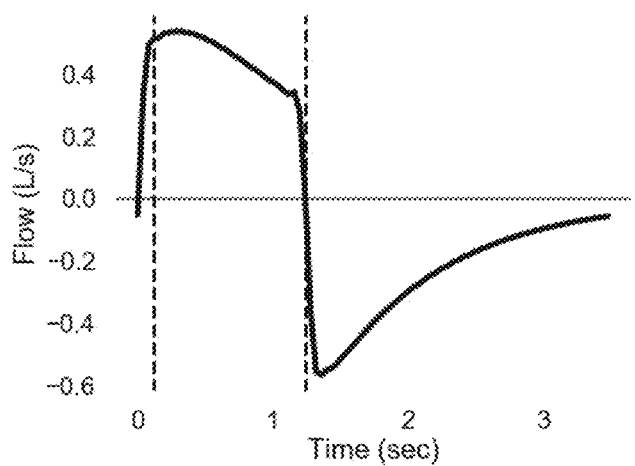
Figure 21C:
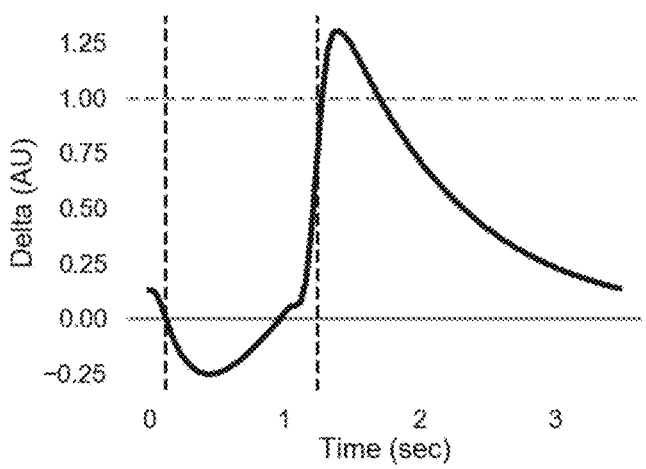
Figure 22A:
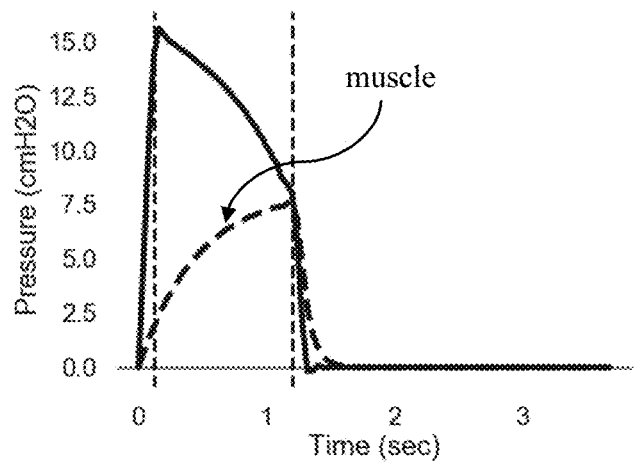
FIGS. 22A to 22C are waveforms that depict an example set of pressure (FIG. 22A), flow (FIG. 22B) and Delta waveform (FIG. 22C) for patient effort in sync with ventilator cycling in volume control ventilation mode.
Figure 22B:
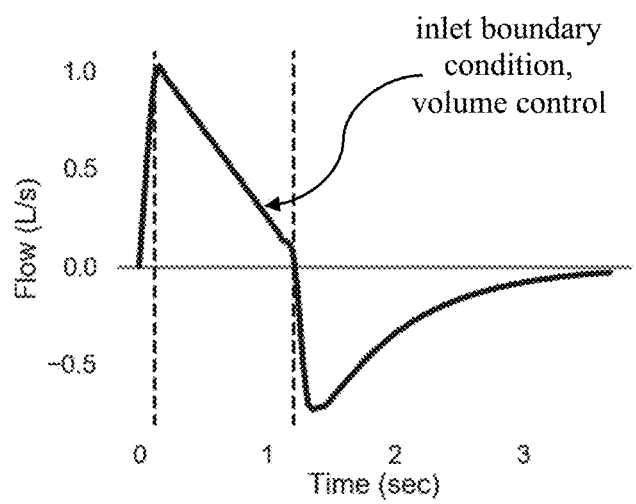
Figure 22C:
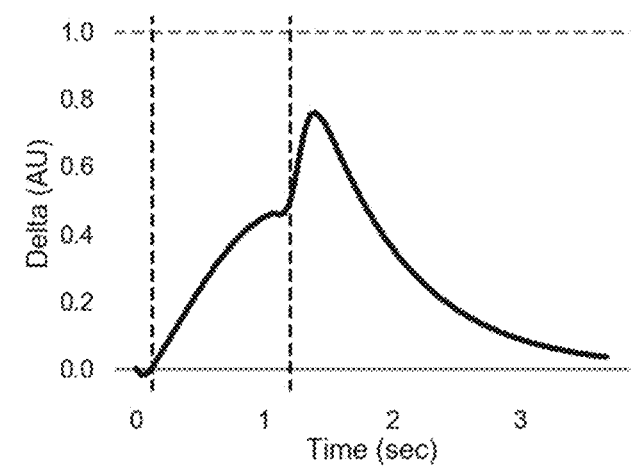

In an embodiment for modeling delayed termination, an inlet ventilator waveform can be prescribed such that its cycling off time (i.e., time at which inspiratory phase ends and expiratory phase begins) exceeds the time at which the muscle pressure begins to relax from its peak value, as depicted in FIG. 10B. In an embodiment to simulate cases of premature termination, an inlet ventilator waveform can be prescribed such that its cycling off time precedes the time at which the muscle pressure begins to relax, as depicted in FIG. 9B. In other embodiments, the time at which the muscle pressure profile rises above its baseline value can be varied to further simulate respiratory muscle activation occurring any time within the breath cycle, for instance, as shown in FIG. 12A whereby the muscle profile rises above baseline about 0.2 seconds into the breath cycle. In an embodiment to simulate cases with neither premature termination nor delayed termination, the muscle waveform can be nullified to simulate a passive patient without respiratory muscle activity, as shown in FIG. 11A. In other embodiments to simulate cases of synchronized muscle and ventilator assist, the cycling off time of the ventilator, as defined by the prescribed inlet boundary condition, can be set to about the time that the muscle profile starts to decay (relax), as shown in FIG. 12A. Other variations to the peak values of the muscle profile as well as inlet boundary conditions can be made without departing form the spirit of generating synthetic waveforms depicting various cycling asynchronies.

An extensive database can be populated with a plurality of synthetic waveforms. In alternative embodiments, stochastic perturbations can further be superimposed upon the synthetic waveforms to simulate sensor and/or process noise.

For each individual breath cycle contained within the database of synthetic waveforms, features such as those discussed in Section Feature Extraction from the Delta Waveform are extracted and deposited into a database containing synthetic feature vectors, one vector for each synthetic breath cycle. Since asynchrony type corresponding to each simulation scenario is known by design, ground truth labels for asynchrony types are known.

In another embodiment, additional synthetic data is generated by use of generative statistical models based upon features previously extracted from synthetic waveforms. Probability distributions can be placed over the extracted features that are conditioned upon the known ground truth labels (i.e., asynchrony type). Upon sampling from the probability distributions, additional synthetic feature vector can be generated and entries can be added to the database of synthetic feature vectors to further augment the amount of data available for training machine learning algorithms or tuning classifiers. A machine learning algorithm can then be trained on the database of synthetic feature vectors using the ground truth labels as the target classification in a similar manner as previously described when real labeled patient data is used for training.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention. It is noted that where a range of values is provided in this specification, each value between the upper and lower limits of that range is also specifically disclosed. The upper and lower limits of these smaller ranges may independently be included or excluded in the range as well. The singular forms "a", "an", and "the" include plural referents unless the context clearly dictates otherwise. It is intended that the specification and examples be considered as exemplary in nature and that variations that do not depart from the essence of the invention fall within the scope of the invention.

The invention claimed is:

1. A system for detecting patient-ventilator interaction comprising:
    a detection module comprising computer-executable instructions stored on a non-transitory computer-readable storage medium in operable communication with one or more computer processors, the detection module configured for and in operable communication with a ventilator for acquiring mechanical ventilator airway pressure and flow waveform data; and
    a patient-ventilator interaction indicator module in operable communication with the detection module, the patient-ventilator interaction indicator module comprising computer-executable instructions stored on a non-transitory computer-readable storage medium in operable communication with one or more of the computer processors for:
        generating a patient-ventilator interaction indicator waveform comprising a Delta waveform from said ventilator waveform data, wherein the Delta waveform represents the difference between normalized pressure, after correcting for positive end expiratory pressure (PEEP), and normalized flow waveforms;
        extracting a set of features from said patient-ventilator interaction indicator waveform; and
        determining and indicating a type of patient-ventilator asynchrony present, or absence thereof, associated with one or more breath cycles, which patient-ventilator asynchrony or absence thereof is based on the extracted set of features.

2. The system of claim 1, wherein the detection module is configured for acquiring the ventilator waveform data directly or indirectly from a mechanical ventilator, directly or indirectly from another monitor or system for producing the ventilator waveform data, or directly or indirectly from an archive of in vivo, ex vivo, in vitro and/or in silico data.

3. The system of claim 2, wherein one or more of the computer processors is embedded in the mechanical ventilator, or another monitor or system or a networked computer system.

4. The system of claim 1, wherein the patient-ventilator interaction module further generates an asynchrony index based on the type of patient-ventilator asynchrony present or absence thereof.

5. The system of claim 1, wherein the Delta waveform is defined as:

$$\delta(t) = \frac{p_{aw}(t) - p_e}{p_{aw}(t^*) - p_e} - \frac{q(t)}{q(t^*)}, t \geq t_0,$$

where t is time, $t_0$ is the time at the start of the breath cycle, $p_e$ is positive end expiratory pressure (PEEP), $p_{aw}$ is airway pressure, q is air flow, and t* is time of maximum flow (q(t)≤q(t*), t≥$t_0$).

6. The system of claim 1, wherein the Delta waveform is defined as:

$$\delta(t) = \frac{p_{aw}(t) - p_e}{p_{aw}(t^{}) - p_e} - \frac{q(t)}{q(t^{})}, t \geq t_0,$$

where t is time, $t_0$ is the time at the start of the breath cycle, $p_e$ is positive end expiratory pressure (PEEP), $p_{aw}$ is airway pressure, q is air flow, t** is a time between to and t*, and t* is time of maximum flow (q(t)≤q(t*), t≥$t_0$).

7. The system of claim 1, wherein the extracting of the set of features comprises extracting one or more of the following features:
    depth of valleys of the Delta waveform;
    maximum value of the Delta waveform within inspiration phase;
    area under the curve of the Delta waveform within inspiration phase;
    maximum cross-correlation of the Delta waveform with a delivered tidal volume waveform;
    area under the portion of the Delta waveform occurring within approximately the first third of the Delta waveform duration;
    maximum value of the Delta waveform occurring within approximately the first third of the Delta waveform duration; and
    locations of valleys of the Delta waveform.

8. The system of claim 1, wherein the computer-executable instructions for determining and indicating the type of patient-ventilator asynchrony present, or absence thereof, comprise a rule-based algorithm configured to classify one or more of the breath cycles into one or more categories of patient-ventilator asynchrony.

9. The system of claim 8, wherein the rule-based algorithm classifies one or more of the breath cycles into the one or more categories of patient-ventilator asynchrony by comparing at least one value from the set of features with a predetermined threshold.

10. The system of claim 1, wherein the computer-executable instructions for determining and indicating the type of patient-ventilator asynchrony present, or absence thereof, comprise a machine-learning classifier trained with patient data and/or synthetic data and configured to classify one or more of the breath cycles into one or more categories of patient-ventilator asynchrony.

11. The system of claim 10, wherein the machine-learning classifier classifies one or more of the breath cycles into the one or more categories of patient-ventilator asynchrony by comparing at least one value from the set of features with a predetermined threshold.

12. The system of claim 10, wherein the synthetic data is derived from in vitro, in silico, or both in vitro and in silico representation of a respiratory system interacting with a mechanical ventilator.

13. The system of claim 1, further including a graphical user interface comprising:
- at least one window for displaying detection of one or more patient-ventilator asynchrony;
- one or more elements within the at least one window for communicating the detected patient-ventilator asynchrony.

14. The system of claim 1, further including a transmission module comprising computer-executable instructions stored on a non-transitory computer storage medium, which transmission module is configured for operable communication with a suitable network protocol to transmit the determined and indicated type of patient-ventilator asynchrony or absence thereof to a remote server and/or smartphone and/or tablet.

15. The system of claim 14, wherein the patient-ventilator interaction module further generates an asynchrony index based on the type of patient-ventilator asynchrony present or absence thereof and the transmission module transmits a notification to a user when the asynchrony index exceeds a pre-determined threshold.

16. The system of claim 1, wherein the types of patient-ventilator asynchrony comprise one or more of inadequate ventilator support, double triggering, ineffective triggering, premature termination, delayed termination, flow starvation, air trapping, buildup of fluid in lungs and/or a ventilator circuit, and/or no asynchrony.

17. The system of claim 1, wherein the computer-executable instructions for determining and indicating the type of patient-ventilator asynchrony present, or absence thereof, comprise a cascade of classifiers configured to classify one or more of the breath cycles into one or more categories of patient-ventilator asynchrony.

18. The system of claim 1, further including a graphical user interface comprising:
- at least one window for displaying detection of one or more patient-ventilator asynchrony; one or more elements within the at least one window comprising one or more recommendations for mitigating the detected patient-ventilator asynchrony.

19. The system of claim 1, further including a graphical user interface comprising:
- at least one window for displaying detection of one or more patient-ventilator asynchrony; one or more elements within the at least one window comprising educational information on the detected patient-ventilator asynchrony.

20. The system of claim 1, further including a graphical user interface comprising:
- at least one window for displaying detection of one or more patient-ventilator asynchrony; one or more elements within the at least one window for communicating an asynchrony index.

* * * * *